US010856821B2

(12) United States Patent
Onobori et al.

(10) Patent No.: US 10,856,821 B2
(45) Date of Patent: Dec. 8, 2020

(54) RADIATION-IRRADIATION DEVICE INCLUDING A CRADLE THAT SUPPORTS AN EDGE PORTION OF A RADIATION DETECTOR

(71) Applicant: FUJIFILM Corporation, Tokyo (JP)

(72) Inventors: Noriyuki Onobori, Kanagawa (JP); Kenji Takata, Kanagawa (JP); Yasuhisa Nozawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 231 days.

(21) Appl. No.: 15/855,390

(22) Filed: Dec. 27, 2017

(65) Prior Publication Data

US 2018/0116615 A1 May 3, 2018

Related U.S. Application Data

(63) Continuation of application No. PCT/JP2016/002487, filed on May 23, 2016.

(30) Foreign Application Priority Data

Jul. 31, 2015 (JP) .................................. 2015-151641
Nov. 19, 2015 (JP) .................................. 2015-226204

(51) Int. Cl.
*A61B 6/00* (2006.01)

(52) U.S. Cl.
CPC .............. *A61B 6/4405* (2013.01); *A61B 6/42* (2013.01); *A61B 6/4208* (2013.01);
(Continued)

(58) Field of Classification Search
CPC ....... A61B 6/42; A61B 6/4208; A61B 6/4283; A61B 6/44; A61B 6/4405; A61B 6/4411;
(Continued)

(56) References Cited

U.S. PATENT DOCUMENTS 7,016,467 B2 *   3/2006   Brooks ................ A61B 6/4405
                                                        378/102
7,097,355 B2 *   8/2006   Araki ................... A61B 6/4283
                                                        378/167
(Continued)

FOREIGN PATENT DOCUMENTS

CN   102283660 A   12/2011
CN   202589542 U   12/2012
(Continued)

OTHER PUBLICATIONS

English translation of JP2011-160913 (A) at Patent Translate on Oct. 23, 2019.*

(Continued)

*Primary Examiner* — Allen C. Ho
(74) *Attorney, Agent, or Firm* — Sughrue Mion, PLLC

(57) ABSTRACT

A radiation-irradiation device includes a leg unit, a radiation source unit, an arm unit that supports the radiation source unit, and a body unit that is an arm support unit supporting the arm unit. Further, radiation-irradiation device includes a cradle that supports one edge portion of a radiation detector detecting radiation and having the shape of a rectangular flat plate and is mounted on the body unit so as to be movable between a first position at which the radiation detector (80) is held along a flat surface of the body unit and a second position at which at least an opposite edge portion of the radiation detector opposite to the one edge portion of the radiation detector is held at a position away from the body unit.

18 Claims, 11 Drawing Sheets

(52) U.S. Cl.
CPC .............. *A61B 6/4283* (2013.01); *A61B 6/44* (2013.01); *A61B 6/4411* (2013.01); *A61B 6/4423* (2013.01); *A61B 6/4429* (2013.01); *A61B 6/4452* (2013.01); *A61B 6/4458* (2013.01)

(58) Field of Classification Search
CPC .... A61B 6/4429; A61B 6/4452; A61B 6/4458
USPC .......................................... 378/189, 196–198
See application file for complete search history.

(56) References Cited

U.S. PATENT DOCUMENTS

| | | | | |
|---|---|---|---|---|
| 7,137,735 B2* | 11/2006 | Araki | A61B 6/4283 | 378/167 |
| 7,575,373 B2* | 8/2009 | Xu | A61B 6/00 | 378/169 |
| 7,785,005 B2* | 8/2010 | Bettouyashiki | G03B 42/025 | 320/107 |
| 7,852,985 B2* | 12/2010 | Liu | G01T 1/175 | 250/370.08 |
| 7,857,511 B2* | 12/2010 | Hesl | A61B 6/4233 | 378/189 |
| 7,866,163 B2* | 1/2011 | Ertel | G01T 1/2928 | 62/3.2 |
| 7,924,982 B2* | 4/2011 | Watanabe | A61B 6/00 | 378/114 |
| 8,174,358 B2* | 5/2012 | Butzine | A61B 6/544 | 340/8.1 |
| 8,292,504 B2* | 10/2012 | Bettouyashiki | G03B 42/025 | 320/107 |
| 8,319,506 B2* | 11/2012 | Liu | A61B 6/4283 | 324/691 |
| 8,324,585 B2* | 12/2012 | McBroom | A61B 6/4233 | 250/370.09 |
| 8,325,875 B2* | 12/2012 | Omernick | A61B 6/42 | 378/62 |
| 8,364,241 B2* | 1/2013 | Hannon | A61B 6/4494 | 378/114 |
| 8,591,106 B2* | 11/2013 | Nishino | A61B 6/4233 | 378/189 |
| 8,616,766 B2* | 12/2013 | Takahashi | G03B 42/04 | 378/189 |
| 8,622,614 B2* | 1/2014 | Carmichael | A61B 6/4266 | 378/198 |
| 8,678,649 B2* | 3/2014 | Bechard | A61B 6/00 | 378/198 |
| 8,714,817 B2* | 5/2014 | Oyaizu | G03B 42/047 | 378/189 |
| 8,721,176 B2* | 5/2014 | McBroom | A61B 6/56 | 378/189 |
| 8,723,131 B2* | 5/2014 | Kobayashi | G03B 42/02 | 250/370.01 |
| 8,834,022 B2* | 9/2014 | Koyanagi | A61B 6/56 | 250/370.09 |
| 8,840,304 B2* | 9/2014 | Perez Zarate | A61B 6/447 | 378/198 |
| 8,848,872 B2* | 9/2014 | Lee | A61B 6/4494 | 250/370.09 |
| 8,861,678 B2* | 10/2014 | Liu | H05G 1/08 | 378/91 |
| 8,891,733 B2* | 11/2014 | Liu | A61B 6/42 | 378/91 |
| 8,899,831 B2* | 12/2014 | Yoshida | A61B 6/4233 | 250/370.08 |
| 8,956,045 B2* | 2/2015 | Tajima | A61B 6/4283 | 378/145 |
| 8,961,011 B2* | 2/2015 | Lalena | A61B 6/4405 | 378/197 |
| 8,975,868 B2* | 3/2015 | Konkle | H02J 7/0027 | 320/115 |
| 9,041,351 B2* | 5/2015 | Ikegame | H02J 7/0045 | 320/107 |
| 9,050,059 B2* | 6/2015 | Kuwabara | A61B 6/542 | |
| 9,055,911 B2* | 6/2015 | Sakuragi | A61B 6/4405 | |
| 9,078,597 B2* | 7/2015 | Patil | A61B 6/4429 | |
| 9,084,582 B2* | 7/2015 | Omura | A61B 6/547 | |
| 9,101,316 B2* | 8/2015 | Liu | A61B 6/4233 | |
| 9,125,611 B2* | 9/2015 | Eaves | A61B 6/4405 | |
| 9,204,855 B2* | 12/2015 | Tsubota | H04W 76/10 | |
| 9,295,438 B2* | 3/2016 | Omura | A61B 6/463 | |
| 9,320,483 B2* | 4/2016 | Kobayashi | A61B 6/00 | |
| 9,326,747 B2* | 5/2016 | Omura | A61B 6/54 | |
| 9,402,592 B2* | 8/2016 | Garcia | A61B 6/4283 | |
| 9,413,961 B2* | 8/2016 | Welsh | A61B 6/4405 | |
| 9,414,794 B2* | 8/2016 | Kaku | A61B 6/4405 | |
| 9,414,795 B2* | 8/2016 | Nakata | A61B 6/4429 | |
| 9,414,802 B2* | 8/2016 | Urbon | A61B 6/4283 | |
| 9,456,799 B2* | 10/2016 | Chicchetti | A61B 6/563 | |
| 9,462,990 B2* | 10/2016 | Kuwabara | A61B 6/542 | |
| 9,492,137 B2* | 11/2016 | Iwamoto | A61B 6/4283 | |
| 9,498,173 B2* | 11/2016 | Yamada | A61B 6/465 | |
| 9,521,983 B2* | 12/2016 | Jang | A61B 6/4429 | |
| 9,521,986 B2* | 12/2016 | Ozawa | A61B 6/4283 | |
| 9,538,978 B2* | 1/2017 | Makino | G16H 40/63 | |
| 9,561,013 B2* | 2/2017 | Tsuchiya | A61B 6/4458 | |
| 9,649,080 B2* | 5/2017 | Kwak | A61B 6/4429 | |
| 9,655,575 B2* | 5/2017 | Park | A61B 6/4233 | |
| 9,668,706 B2* | 6/2017 | Kim | A61B 6/547 | |
| 9,668,707 B2* | 6/2017 | Watanabe | A61B 6/56 | |
| 9,668,708 B2* | 6/2017 | Okuno | A61B 6/447 | |
| 9,675,309 B2* | 6/2017 | Kim | A61B 6/4266 | |
| 9,693,746 B2* | 7/2017 | Ancar | A61B 6/08 | |
| 9,700,278 B2* | 7/2017 | Tezuka | A61B 6/563 | |
| 9,730,658 B2* | 8/2017 | Tajima | H04N 5/32 | |
| 9,778,380 B2* | 10/2017 | Enomoto | G01T 1/161 | |
| 9,788,810 B2* | 10/2017 | Ancar | A61B 6/487 | |
| 9,848,841 B2* | 12/2017 | Choi | A61B 6/4405 | |
| 9,855,017 B2* | 1/2018 | Wojcik | A61B 6/4233 | |
| 9,931,089 B2* | 4/2018 | Nariyuki | A61B 6/107 | |
| 9,949,702 B2* | 4/2018 | Nam | A61B 6/4291 | |
| 9,955,931 B2* | 5/2018 | Bettouyashiki | A61B 6/4283 | |
| 9,968,315 B2* | 5/2018 | Ogura | A61B 6/4283 | |
| 10,058,303 B2* | 8/2018 | Shimohira | A61B 6/06 | |
| 10,064,588 B2* | 9/2018 | Uchida | A61B 6/4405 | |
| 10,104,311 B2* | 10/2018 | Takekoshi | G06T 7/0012 | |
| 10,105,114 B2* | 10/2018 | Shimizukawa | A61B 6/4283 | |
| 10,219,764 B2* | 3/2019 | Yang | A61B 6/4266 | |
| 10,258,307 B2* | 4/2019 | Park | A61B 6/547 | |
| 10,263,339 B2* | 4/2019 | Kim | H01Q 9/42 | |
| 10,271,805 B2* | 4/2019 | Koyanagi | A61B 6/56 | |
| 10,278,668 B2* | 5/2019 | Hishikawa | A61B 6/467 | |
| 10,335,111 B2* | 7/2019 | Enomoto | A61B 6/56 | |
| 10,338,238 B2* | 7/2019 | Kim | A61B 6/4283 | |
| 10,368,823 B2* | 8/2019 | Uchiyama | A61B 6/56 | |
| 10,433,805 B2* | 10/2019 | Hishida | A61B 6/06 | |
| 10,456,100 B2* | 10/2019 | Ninomiya | A61B 6/4405 | |
| 10,506,995 B2* | 12/2019 | Ninomiya | A61B 6/547 | |
| 10,660,584 B2* | 5/2020 | Tajima | A61B 6/461 | |
| 10,667,772 B2* | 6/2020 | Mikami | A61B 90/50 | |
| 10,674,977 B2* | 6/2020 | Nabeta | A61B 6/4458 | |
| 10,709,406 B2* | 7/2020 | Aoshima | A61B 6/12 | |
| 2004/0066899 A1 | 4/2004 | Araki et al. | | |
| 2006/0070384 A1 | 4/2006 | Ertel | | |
| 2011/0286575 A1 | 11/2011 | Omernick et al. | | |
| 2014/0098941 A1 | 4/2014 | Konkle et al. | | |

FOREIGN PATENT DOCUMENTS

| | | |
|---|---|---|
| CN | 103705257 A | 4/2014 |
| DE | 10 2011 082607 A1 | 3/2013 |
| EP | 2 878 264 A1 | 6/2015 |
| JP | 2006102492 A | 4/2006 |
| JP | 2006296676 A | 11/2006 |
| JP | 2011160913 A | 8/2011 |
| JP | 2011245291 A | 12/2011 |
| JP | 2012029889 A | 2/2012 |
| JP | 2012170634 A | 9/2012 |
| JP | 2014076354 A | 5/2014 |

(56) References Cited

FOREIGN PATENT DOCUMENTS

| JP | 2014147465 A | 8/2014 |
| JP | 2014-204823 A | 10/2014 |
| JP | 2015051052 A | 3/2015 |

OTHER PUBLICATIONS

"Portable X-ray Equipment IPF-21: Inverter Type", Toshiba Medical Supply Co., Ltd., Search on Apr. 3, 2015, [online] <URL:http://www.toshiba-medical.co.jp/tmd/products/xray/mobile/ipf21/index.html> (4 pages ).
Written Opinion, dated Sep. 6, 2016 from the International Searching Authority in counterpart International application No. PCT/JP2016/002487.
International Preliminary Report on Patentability, dated Feb. 6, 2018, from the International Bureau in counterpart International application No. PCT/JP2016/002487.
International Search Report, dated Sep. 6, 2016 from the International Searching Authority in counterpart International application No. PCT/JP2016/002487.
Supplemental European Search Report dated Sep. 3, 2018, issued by European Patent Office for EP 16832444.0.
Communication dated Mar. 27, 2020, from the State Intellectual Property Office of the P.R.C in application No. 201680038024.3.

\* cited by examiner

RADIATION-IRRADIATION DEVICE INCLUDING A CRADLE THAT SUPPORTS AN EDGE PORTION OF A RADIATION DETECTOR

CROSS REFERENCE TO RELATED APPLICATIONS

The present application is a Continuation of PCT International Application No. PCT/JP2016/002487 filed on May 23, 2016, which claims priority under 35 U.S.C. § 119(a) to Japanese Patent Application No. 2015-151641 filed on Jul. 31, 2015 and Japanese Patent Application No. 2015-226204 filed on Nov. 19, 2015. Each of the above applications is hereby expressly incorporated by reference, in its entirety, into the present application.

BACKGROUND

Technical Field

The present invention relates to a radiation-irradiation device that irradiates a subject with radiation in a case in which the radiation image of the subject is to be acquired.

Background Art

In the past, a portable radiation-irradiation device, on which only a minimum number of components for radiation irradiation, such as a radiation source and an electrical circuit, are mounted and which can be operated while being held with hands by an operator, has been proposed as disclosed in, for example, JP2012-029889A and "Toshiba Medical Supply Co., Ltd., X-ray equipment IPF-21, [online], [Search on Apr. 3, 2015], Internet <URL: http://www.toshiba-medical.co.jp/tmd/products/xray/mobile/ipf21/index.html>". Since this kind of portable radiation-irradiation device is reduced in weight so that an operator can hold and operate the radiation-irradiation device with hands, the radiation-irradiation device is advantageous for the imaging of a subject in various directions.

A radiation detector (so-called "Flat Panel Detector"), which records a radiation image representing a subject by being irradiated with radiation transmitted through the subject, is generally used in a case in which the radiation image of the subject is to be taken by this kind of radiation irradiation device. A cassette-type radiation detector having a structure in which an image detection unit and a control unit, such as a battery for drive and an electrical circuit relating to drive, are received in a housing is well known as the radiation detector. Further, in a case in which such a radiation detector is disposed at a position facing the radiation-irradiation device with a subject interposed therebetween and the radiation-irradiation device is driven in this state, the radiation detector is irradiated with radiation transmitted through the subject. Accordingly, a radiation image represented by the radiation transmitted through the subject is acquired.

The portable radiation-irradiation device can be held and operated with hands by an operator. However, a radiation-irradiation device, which includes a support device supporting a radiation source unit including a radiation source, is proposed to prevent shaking and to prevent the operator's hands or the like from being exposed to radiation. "Toshiba Medical Supply Co., Ltd., X-ray equipment IPF-21, [online], [Search on Apr. 3, 2015], Internet <URL:http://www-.toshiba-medical.co.jp/tmd/products/xray/mobile/ipf21/index.html>" also discloses an example of such a support device, and particularly, a support device that includes wheel parts provided at lower portions of support legs and can travel.

The radiation-irradiation device including the support device basically includes: a leg unit that is adapted to be capable of traveling using wheels; a body unit that receives a control unit including a battery for the drive of a radiation source, an electrical circuit relating to the drive of the radiation source, and the like and is held on the leg unit; and an arm unit that is connected to the body unit. The radiation source unit is mounted on the distal end of the arm unit.

In a case in which the radiation-irradiation device is in use, first, the radiation-irradiation device is moved close to a bed for a patient. After that, the radiation source unit is moved to a desired position, and the radiation detector is moved to a desired position behind the subject. Then, the radiation source unit is moved to a desired position above the subject in this state, the radiation source unit is driven to irradiate the subject with radiation, radiation transmitted through the subject is detected by the radiation detector, and the radiation image of the subject is acquired.

Since the radiation detector is required for taking the radiation image, an operator needs to carry the radiation detector in a case in which the operator moves the radiation-irradiation device. For this reason, a radiation-irradiation device, which can receive a radiation detector, is proposed. For example, a radiation-irradiation device including a storage container, which can receive a plurality of radiation detectors and can charge the radiation detectors, is proposed in JP2006-102492A. Further, a radiation-irradiation device including a holder, which holds one edge portion of a rectangular radiation detector and horizontally holds the other three edge portions of the radiation detector in a state in which the other three edge portions of the radiation detector are opened, is proposed in JP2015-51052A. Since the radiation detector is provided with a generator unit that generates electric power by ultraviolet rays and a capacitor unit that stores generated electric power and the device is provided with an ultraviolet irradiation unit, the device disclosed in JP2015-51052A is adapted to be capable of charging and sterilizing the radiation detector at the same time by irradiating the radiation detector with ultraviolet rays. Further, since the three edge portions of the radiation detector are opened, a contamination preventive bag for preventing the contamination of the radiation detector can be easily mounted on the radiation detector.

SUMMARY OF THE INVENTION

However, since the device disclosed in JP2006-102492A can receive the plurality of radiation detectors, the size of the storage container is increased. Further, the size of the holder is increased in a case in which the radiation detector is horizontally held as in the device disclosed in JP2015-51052A. Since the size of the radiation-irradiation device is increased in a case in which the size of a portion receiving the radiation detector is large as described above, it is difficult to perform imaging in a small radius.

The invention has been made in consideration of the above-mentioned circumstances, and an object of the invention is to provide a radiation-irradiation device that can perform imaging in a small radius while receiving a radiation detector.

A radiation-irradiation device according to the invention comprises a leg unit that is capable of traveling on a device-placement surface, a radiation source unit that generates radiation, an arm unit on which the radiation source unit is mounted, a body unit to which the arm unit is connected and which is held by the leg unit and includes a flat surface on a side thereof opposite to a side to which the arm unit is connected, and a detector holder that supports one edge portion of a radiation detector detecting the radiation and having the shape of a rectangular flat plate and is mounted on the body unit so as to be movable between a first position at which the radiation detector is held along the flat surface of the body unit and a second position at which at least an opposite edge portion of the radiation detector opposite to the one edge portion of the radiation detector is held at a position away from the body unit.

"Flat surface" means the surface of the body unit that is positioned on the outermost side on the side of the body unit opposite to the side of the body unit to which the arm unit is connected.

"Shape of a rectangular flat plate" means the shape of a flat plate which corresponds to the shape of a rectangular detection region of the radiation detector and of which four linear edge portions cross each other so as to be orthogonal to each other. However, in the invention, the shape of the radiation detector is included in the shape of a rectangular flat plate as long as the other three edge portions of the radiation detector cross each other so as to be substantially orthogonal to each other even though one edge portion of the radiation detector does not have the shape of a straight line due to a handle formed on one edge portion of the radiation detector or a notch or a protruding portion formed on one edge portion of the radiation detector.

"Position away" means a position at which at least an opposite edge portion of the radiation detector opposite to one edge portion of the radiation detector is farther away from the body unit than the first position and which is away from the body unit so that the contamination preventive bag can cover the radiation detector from the opposite edge portion of the radiation detector to the vicinity of one edge portion where the radiation detector is supported.

"The radiation detector is held along the flat surface of the body unit" means a state in which the radiation detector is held so as to be substantially parallel to the flat surface. In a state in which the radiation detector is held, the surface of the radiation detector facing the body unit may be positioned outside the flat surface of the body unit, may be positioned closer to the inside of the body unit than the flat surface, and may correspond to the flat surface. Further, the surface of the radiation detector opposite to the surface of the radiation detector facing the body unit may be positioned inside the flat surface of the body unit and may correspond to the flat surface.

In the radiation-irradiation device according to the invention, the detector holder may hold the radiation detector so that the one edge portion is positioned on a lower side in a vertical direction and the opposite edge portion of the radiation detector is positioned on an upper side in the vertical direction.

Further, in the radiation-irradiation device according to the invention, the length of the body unit in a direction orthogonal to the flat surface may be shorter than the length of the body unit in a direction parallel to the flat surface.

"Direction parallel to the flat surface" means an arbitrary direction parallel to the flat surface.

Furthermore, in the radiation-irradiation device according to the invention, the detector holder may hold the radiation detector at least inside the flat surface at the first position.

"At least inside" includes not only a state in which a part of the radiation detector is received inside the surface of the flat surface but also a state in which the surface of the radiation detector opposite to the surface of the radiation detector facing the body unit is received inside the surface of the flat surface and a state in which the surface of the radiation detector opposite to the surface of the radiation detector facing the body unit corresponds to the surface of the flat surface. As long as "inside" of "at least inside" is the inside of the flat surface, "inside" of "at least inside" may be any one of the inside and outside of the housing of the body unit.

Moreover, in the radiation-irradiation device according to the invention, the detector holder may be mounted on the body unit so as to be rotationally movable about a rotational movement axis parallel to a direction in which the one edge portion extends.

Further, in the radiation-irradiation device according to the invention, the detector holder may be mounted on the body unit so as to be movable in a direction orthogonal to a direction in which the one edge portion extends.

Furthermore, in the radiation-irradiation device according to the invention, the detector holder may include a connector that is to be electrically connected to the radiation detector to charge the radiation detector.

In this case, the connector may be electrically connected to the radiation detector at least at the first position, and electrical connection between the connector and the radiation detector may be released at least at the second position.

"Electrically connected to the radiation detector at least at the first position" includes not only electrical connection between the connector and the radiation detector at the first position but also electrical connection between the connector and the radiation detector at a position other than the first position.

"Electrical connection between the connector and the radiation detector is released at least at the second position" includes not only the release of the electrical connection between the connector and the radiation detector at the second position but also the release of the electrical connection between the connector and the radiation detector at a position other than the second position.

Further, in the radiation-irradiation device according to the invention, the detector holder may be detachably mounted on the body unit.

Furthermore, in the radiation-irradiation device according to the invention, the detector holder may be subjected to antibacterial treatment.

Moreover, in the radiation-irradiation device according to the invention, the flat surface may be inclined toward a side to which the arm unit is connected.

"The flat surface is inclined toward a side to which the arm unit is connected" means that the flat surface is inclined so as to be close to the side to which the arm unit is connected toward the side opposite to the leg unit from the leg unit. In more detail, "the flat surface is inclined toward a side to which the arm unit is connected" means that, in a case in which a perpendicular perpendicularly extending from the leg unit toward the side opposite to the leg unit is set on the side of the body unit opposite to the side of the body unit to which the arm unit is connected, the flat surface is inclined so as to be away from the perpendicular from the leg unit toward the opposite to the leg unit.

Further, the radiation-irradiation device according to the invention may further comprise a fixing part that fixes the opposite edge portion of the radiation detector to the flat surface in a case in which the detector holder is positioned at the first position.

Here, the fixing part may fix the radiation detector so that the radiation detector is in close contact with the flat surface, and may fix the radiation detector at a position away from the flat surface.

Furthermore, in the radiation-irradiation device according to the invention, the fixing part may be mounted on the flat surface so as to be movable on the flat surface in a vertical direction.

"Vertical direction" means a vertical direction in a case in which the side of the flat surface close to the leg unit is set as the lower side and the side of the flat surface opposite to the leg unit is set as the upper side.

Moreover, the radiation-irradiation device according to the invention may further comprise a locking part that locks the fixing part to restrict the movement of the fixing part.

"Restrict the movement of the fixing part" means that the fixing part is not linearly moved or not rotationally moved from the position at which the fixing part is locked and the radiation detector fixed to the flat surface does not deviate from the fixing part. Here, in a case in which the fixing part is movable on the flat surface in the vertical direction, the radiation detector fixed to the flat surface is adapted not to deviate from the fixing part through the restriction of the movement of the fixing part in the vertical direction in a state in which the fixing part fixes the radiation detector to the flat surface. Locking may be performed using a key, may be performed using a password, or may be performed using the biometric authentication or the like of a fingerprint, the iris, or the like.

Further, in the radiation-irradiation device according to the invention, a cushioning material may be provided on the flat surface at a position facing the radiation detector.

In this case, the cushioning material may be provided at a position facing at least a part of the radiation detector around the radiation detector.

Furthermore, in the radiation-irradiation device according to the invention, the cushioning materials may be provided at a plurality of positions corresponding to sizes of the radiation detectors to be used.

As long as the cushioning material is a material having a function to soften an impact and vibration applied from the outside to make the impact and vibration be not easily transmitted to the radiation detector, an arbitrary material can be used as the cushioning material. For example, rubber, foamed styrol, shock-absorbing gel, and the like can be used as the cushioning material.

Further, "at least a part of the radiation detector around the radiation detector" means at least a part of a frame that has the highest stiffness in the radiation detector and forms the peripheral portion of the radiation detector. Furthermore, the position facing at least a part of the radiation detector may be a position facing the entire peripheral portion of the radiation detector, and may be, for example, a position facing one side portion of the radiation detector, a position facing at least one of four corners of the radiation detector, or positions facing one edge and at least one of four corners of the radiation detector.

Furthermore, the radiation-irradiation device according to the invention may further comprise a biasing part that biases the radiation detector, which is held by the detector holder, along the flat surface in at least one direction orthogonal to the one edge portion of the radiation detector.

In this case, a plurality of biasing parts may be provided so as to correspond to the radiation detectors having a plurality of sizes.

The detector holder of the radiation-irradiation device according to the invention supports one edge portion of the radiation detector having the shape of a rectangular flat plate and is mounted on the body unit so as to be movable between the first position at which the radiation detector is held along the flat surface of the body unit and the second position at which at least an opposite edge portion of the radiation detector opposite to the one edge portion of the radiation detector is held at a position away from the body unit. For this reason, in a case in which the detector holder is moved to the second position, one edge portion of the radiation detector can be supported by the detector holder. After that, in a case in which the detector holder is moved to the first position, the radiation detector is held along the flat surface of the body unit. For this reason, the radiation detector can be held integrally with the body unit. Accordingly, an increase in the size of the device can be prevented while the device receives the radiation detector. Therefore, the device can perform imaging in a small radius while receiving the radiation detector.

Further, in a state in which the detector holder is moved to the second position, the radiation detector is in a state in which only one edge portion of the radiation detector is supported. For this reason, three edge portions of the radiation detector other than the one edge portion of the radiation detector, which is supported by the detector holder, are in an open state. Accordingly, in a state in which the detector holder is moved to the second position, a contamination preventive bag for preventing the contamination of the radiation detector can be easily mounted on the radiation detector.

DESCRIPTION OF THE PREFERRED EMBODIMENTS

Figure 1:
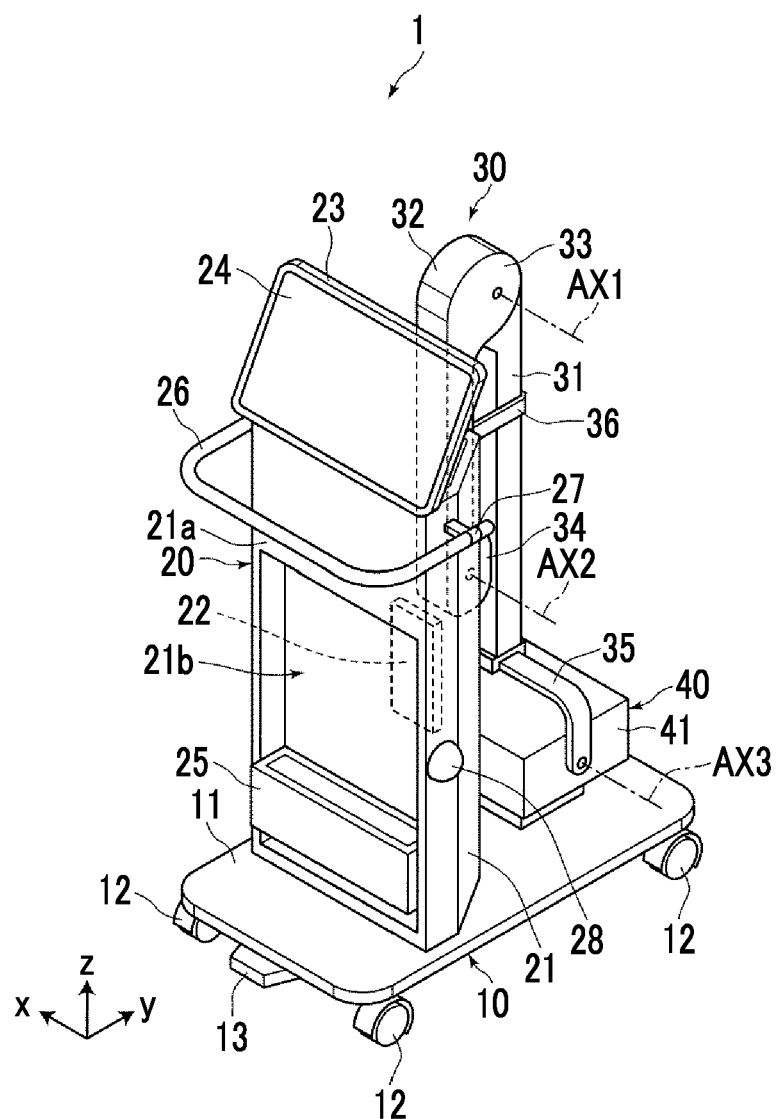
FIG. 1 is a perspective view showing a shape of an entire radiation-irradiation device according to a first embodiment of the invention.
Figure 2:
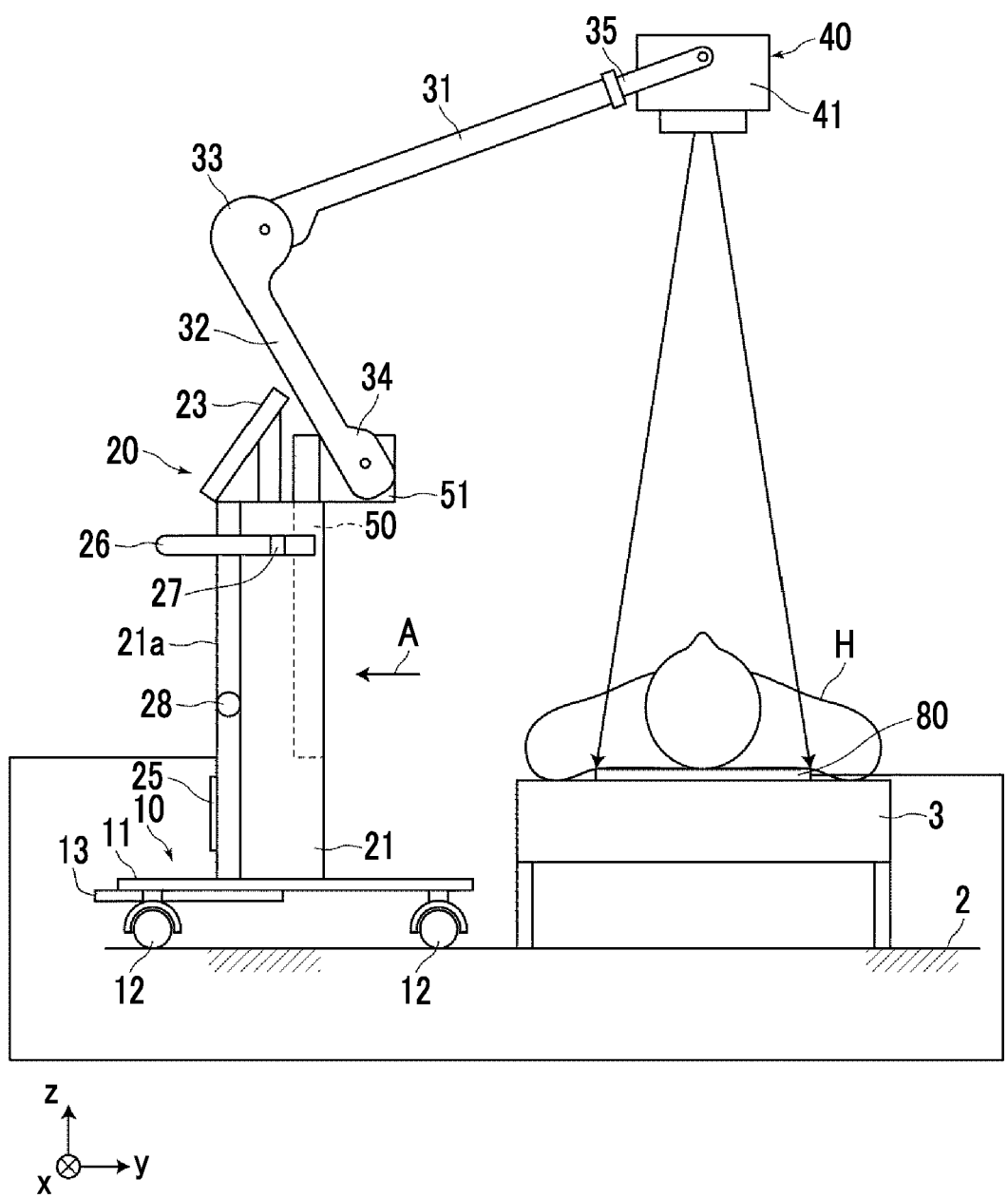
FIG. 2 is a diagram showing a state in which the radiation-irradiation device according to the first embodiment of the invention is in use.

Embodiments of the invention will be described below with reference to the drawings. FIG. 1 is a perspective view showing the shape of the entire radiation-irradiation device according to a first embodiment of the invention that is not in use, and FIG. 2 is a side view showing a state in which the radiation-irradiation device according to the first embodiment of the invention is in use. In the following description, the upper side and the lower side in a vertical direction in a state in which the radiation-irradiation device is placed on a device-placement surface, such as the floor of, for example, a medical facility are referred to as "upper" and "lower", and a direction perpendicular to the vertical direction in the same state as the state is referred to as a "horizontal" direction. Further, a coordinate system in which the vertical direction is a z direction, a lateral direction of FIG. 2 is a y direction, and a direction perpendicular to the plane of FIG. 2 is an x direction is set in the following description.

As shown in FIG. 1, a radiation-irradiation device 1 according to this embodiment includes a leg unit 10, a body unit 20, an arm unit 30, and a radiation source unit 40.

The leg unit 10 can travel on the device-placement surface 2, and includes a plate-like base 11 and four wheel parts 12 that are mounted on four corners of the lower surface of the plate-like base 11. Each of the wheel parts 12 is formed of a rubber tire or the like, and is mounted on the plate-like base 11 so as to be revolvable about an axis, which extends in the vertical direction, in a horizontal plane. Accordingly, the leg unit 10 is adapted to be capable of traveling on the device-placement surface 2 in an arbitrary direction. Further, a connector 13, which is to be connected to a power source, is mounted on the lower surface of the leg unit 10 to charge a radiation detector 80 and the radiation-irradiation device 1 as described below.

The body unit 20 stands on the leg unit 10, and includes a housing 21. A control unit 22, which controls the drive of the radiation-irradiation device 1, and a battery (hereinafter, simply referred to as a control unit 22) are received in the housing 21.

The control unit 22 is a unit that performs control relating to the generation and irradiation of radiation, such as tube current, irradiation time, and a tube voltage of the radiation source unit 40, and control relating to the acquisition of a radiation image, such as image processing for a radiation image acquired by the radiation detector 80. The control unit 22 is composed of, for example, a computer in which a program for control is installed, dedicated hardware, or a combination of both the computer and the dedicated hardware.

Further, a monitor 23 is mounted on the upper surface of the housing 21. Furthermore, a handle 26, which is used to push or pull the radiation-irradiation device 1, is mounted on the upper portion of the housing 21 by an adapter 27. Moreover, omnidirectional cameras 28, which are used to take omnidirectional images of the radiation-irradiation device 1, are mounted on both side surfaces of the body unit 20. Only one omnidirectional camera 28 is shown in FIGS. 1 and 2.

Further, the body unit 20 is adapted so that a radiation detector 80 to be described below can be received in the surface of the body unit 20 opposite to the side on which the arm unit 30 is mounted. A structure that can receive the radiation detector 80 will be described later.

The monitor 23 is formed of a liquid crystal panel or the like, and displays a radiation image that is acquired from the imaging of a subject H and various kinds of information that is required for the control of the radiation-irradiation device 1. Furthermore, the monitor 23 includes a touch panel type input part 24, and receives the input of various commands required for the operation of the radiation-irradiation device 1. Specifically, the monitor 23 receives an input for the setting of imaging conditions and an input for imaging, that is, the emission of radiation. The monitor 23 corresponds to display means. The monitor 23 is mounted on the upper surface of the body unit 20 so that the inclination and the rotational position of the monitor 23 are changeable. Further, the monitor 23 may include buttons, which are used to perform various operations, and the like as the touch panel type input part 24 instead of the touch panel type input part 24.

The arm unit 30 is supported on the body unit 20. In detail, the arm unit 30 is supported on the surface of the body unit 20 opposite to the handle 26, that is, a right surface of the body unit 20 in FIG. 2. The arm unit 30 is adapted to be capable of being raised and lowered relative to the body unit 20 by a raising/lowering mechanism 50. The arm unit 30 includes a first arm 31, a second arm 32, a first rotational moving portion 33, a second rotational moving portion 34, and a mounting part 35. The radiation source unit 40 is connected to the distal end of the first arm 31 by the mounting part 35. In the following description, an end portion of the first arm 31 close to the radiation source unit 40 is referred to as an upper end portion and an end portion of the first arm 31 close to the second arm 32 is referred to as a lower end portion. Further, an end portion of the second arm 32 close to the first arm 31 is referred to as an upper end portion and an end portion of the second arm 32 close to the body unit 20 is referred to as a lower end portion.

The first arm 31 and the second arm 32 are connected to each other by the first rotational moving portion 33 so as to be rotationally movable about a rotational movement axis AX1. The rotational movement axis AX1 is an axis extending in the x direction. The first arm 31 is rotationally moved about the rotational movement axis AX1 so that an angle between the first arm 31 and the second arm 32 is changed. The first rotational moving portion 33 holds both the first arm 31 and the second arm 32 so that the first arm 31 is rotationally moved relative to the second arm 32 through a friction mechanism. For this reason, the first arm 31 is rotationally movable in a case in which an external force, which is strong to some extent, is applied to the first arm 31, and maintains an angle relative to the second arm 32 without being rotationally moved as long as an external force is not applied to the first arm 31.

The second arm 32 is connected to an adapter 51, which is mounted on the upper end portion of the raising/lowering mechanism 50, through the second rotational moving portion 34 so as to be rotationally movable about a rotational movement axis AX2. The rotational movement axis AX2 is an axis extending in the x direction. The second arm 32 is rotationally moved about the rotational movement axis AX2 so that an angle between the second arm 32 and the surface of the body unit 20 on which the arm unit 30 is supported is changed. The second rotational moving portion 34 holds both the second arm 32 and the body unit 20 so that the second arm 32 is rotationally moved relative to the body unit 20 through a friction mechanism. For this reason, the second rotational moving portion 34 is rotationally movable in a case in which an external force, which is strong to some extent, is applied to the second rotational moving portion 34, and maintains an angle relative to the body unit 20 without being rotationally moved as long as an external force is not applied to the second rotational moving portion 34.

Figure 3:
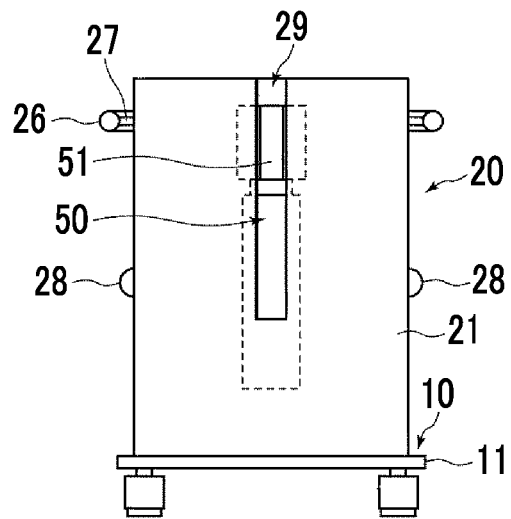
FIG. 3 is a diagram viewed in a direction of arrow A of FIG. 2.

FIG. 3 is a diagram viewed in the direction of arrow A of FIG. 2. As shown in FIG. 3, a groove 29, through which the adapter 51 can pass at the time of an operation for raising and lowering the arm unit 30 performed by the raising/lowering mechanism 50, is formed on the right surface of the body unit 20 in FIG. 2. For illustration, the monitor 23 and the arm unit 30 are not shown in FIG. 3.

The mounting part 35 is formed in a U shape, and is mounted on the distal end of the first arm 31. The radiation source unit 40 is connected to the distal end of the first arm 31 through the mounting part 35 so as to be rotationally movable about a rotational movement axis AX3. The rotational movement axis AX3 is an axis extending in the x direction. The radiation source unit 40 is rotationally moved about the rotational movement axis AX3 so that an angle between the radiation source unit 40 and the first arm 31 is changed. The mounting part 35 holds both the radiation source unit 40 and the first arm 31 so that the radiation source unit 40 is rotationally moved relative to the first arm 31 through a friction mechanism. For this reason, the radiation source unit 40 is rotationally movable in a case in which an external force, which is strong to some extent, is applied to the radiation source unit 40, and maintains an angle relative to the first arm 31 without being rotationally moved as long as an external force is not applied to the radiation source unit 40.

The rotation between the first arm 31 and the second arm 32 and the rotation between the first arm 31 and the radiation source unit 40 are achieved through the friction mechanisms, but the rotational positions of the first arm 31, the second arm 32, and the radiation source unit 40 may be fixed by publicly known lock mechanisms. In this case, the rotation between the first arm 31 and the second arm 32 and the rotation between the first arm 31 and the radiation source unit 40 can be performed in a case in which the lock mechanisms are released. Further, the rotational positions can be fixed in a case in which the lock mechanisms are locked at desired rotational positions.

Here, the arm unit 30 is positioned at the lowest position of the raising/lowering mechanism 50 in a case in which the radiation-irradiation device 1 shown in FIG. 1 is not in use. Further, the rotational position of the arm unit 30 is an initial rotational position.

The initial rotational position is the rotational position of the arm unit 30 in a case in which the first arm 31 and the second arm 32 are folded. Particularly, in this embodiment, the initial rotational position is set to the rotational position of the arm unit 30 in a state in which the first arm 31 and the second arm 32 are folded to the limit where the first arm 31 and the second arm 32 are not rotationally moved any more as shown in FIG. 1. At the initial rotational position, the second arm 32 is rotationally moved so that the first rotational moving portion 33 is positioned above the second rotational moving portion 34.

The first arm 31 and the second arm 32 are connected to each other by a connecting belt 36 at the initial rotational position. For example, one end portion of the connecting belt 36 is mounted on the second arm 32 and a hook-and-loop fastener is mounted on the other end portion of the connecting belt 36. A hook-and-loop fastener corresponding to the hook-and-loop fastener of the connecting belt 36 is mounted on the opposite surface of the first arm 31 in FIG. 1. Further, the connecting belt 36 is put around the first arm 31 from the right surface of the first arm 31 in FIG. 1 to the opposite surface of the first arm 31 to connect the hook-and-loop fastener of the connecting belt 36 to the hook-and-loop fastener mounted on the first arm 31. Accordingly, the first arm 31 is not rotationally moved relative to the second arm 32 at the initial rotational position.

The radiation source unit 40 has a structure where a radiation source, a collimator for narrowing the irradiation range of radiation, and the like are received in a housing 41. The radiation source is composed of, for example, an X-ray tube, a booster circuit, cooling means for cooling the X-ray tube, and the like. The emission of radiation from the radiation source of the radiation source unit 40 is performed by a command that is sent from the input part 24 of the monitor 23 by an operator.

Figure 4:
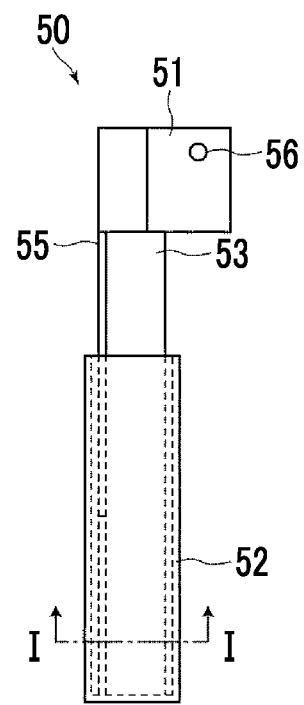
FIG. 4 is a side view showing a structure of a raising/lowering mechanism.
Figure 5:
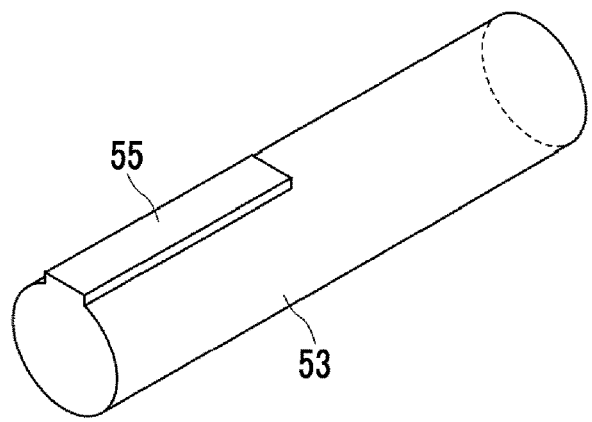
FIG. 5 is a perspective view showing the structure of a shaft.
Figure 6:
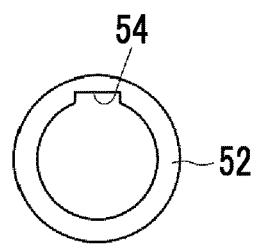
FIG. 6 is a cross-sectional view taken along line I-I of FIG. 4.

FIG. 4 is a side view showing the structure of the raising/lowering mechanism, FIG. 5 is a perspective view showing the structure of a shaft that composes the raising/lowering mechanism, and FIG. 6 is a cross-sectional view taken along line I-I of FIG. 4. As shown in FIG. 4, the raising/lowering mechanism 50 includes an outer cylinder 52 that is mounted inside the body unit 20, a shaft 53 that is fitted to the outer cylinder 52, and the adapter 51 that is mounted on the upper end portion of the shaft 53. A hole 56 is formed in the adapter 51 at a position corresponding to the rotational movement axis AX2 of the second rotational moving portion 34.

The shaft 53 is movable relative to the outer cylinder 52 in the vertical direction, and the position of the shaft 53 relative to the outer cylinder 52 in the vertical direction can be fixed at a desired position by a lock mechanism (not shown).

A key way 54 is formed in the outer cylinder 52, and a key 55 to be engaged with the key way 54 is formed on the shaft 53. The key 55 is formed so as to have a predetermined length from the upper end of the shaft 53. Here, the key 55 has a length that allows the lower end of the key 55 to be positioned above the upper end of the outer cylinder 52 in a state in which the shaft 53 reaches the highest position. For this reason, since the key 55 is engaged with the key way 54 until the shaft 53 reaches the highest position, the shaft 53 is not rotated relative to the outer cylinder 52 about the central axis thereof. However, since the key 55 deviates from the key way 54 in a case in which the shaft 53 reaches the highest position, the shaft 53 is rotatable relative to the outer cylinder 52 about the central axis thereof. Accordingly, the arm unit 30 mounted on the raising/lowering mechanism 50 is revolvable relative to the body unit 20. Revolution means rotation about the axis of the shaft 53, that is, a z axis that is an axis perpendicular to the device-placement surface 2.

In this embodiment, the radiation detector 80 is disposed under a subject H supine on a bed 3 and is irradiated with radiation (for example, X-rays) emitted from the radiation source unit 40 through the subject H as shown in FIG. 2, so that the subject is imaged. The radiation detector 80 and the radiation-irradiation device 1 are connected to each other in a wireless or wired manner. Accordingly, the radiation image of the subject H, which is acquired by the radiation detector 80, is directly input to the device 1.

Figure 7:
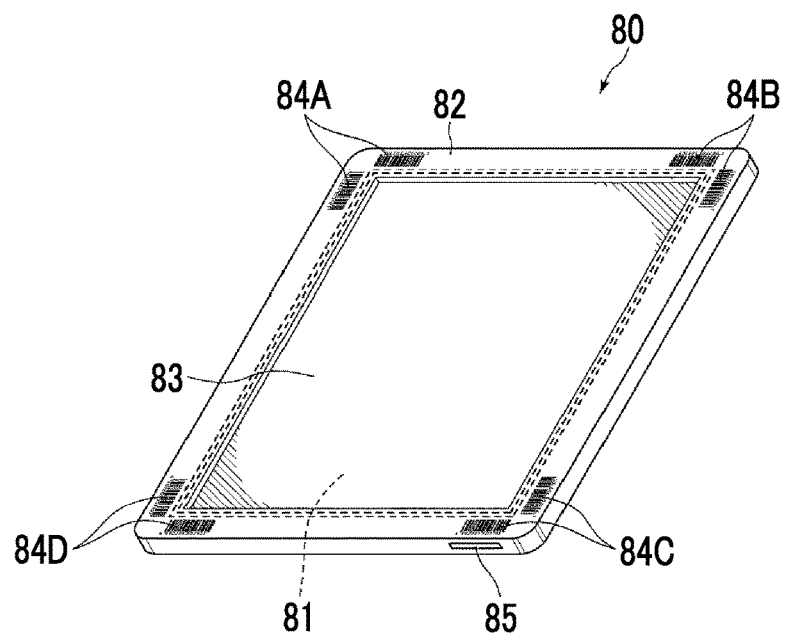
FIG. 7 is a perspective view showing an appearance of a radiation detector viewed from the front surface thereof that is a radiation detecting surface.

The radiation detector 80 will be briefly described here with reference to FIG. 7. FIG. 7 is a perspective view showing the appearance of the radiation detector viewed from the front surface thereof that is a radiation detecting surface. As shown in FIG. 7, the radiation detector 80 has the shape of a rectangular flat plate and is a cassette-type radiation detector that includes a housing 82 receiving an image detection unit 81. As well known, the image detection unit 81 includes a scintillator (phosphor) that converts incident radiation into visible light and a thin-film-transistor (TFT) active matrix substrate. A rectangular imaging region in which a plurality of pixels for accumulating electric charges corresponding to visible light emitted from the scintillator are arranged is formed on the TFT active matrix substrate.

The housing 82 includes a frame which is made of metal and of which four corners are subjected to round chamfering, and an imaging control unit and the like are built in the housing 82 in addition to the image detection unit 81. The imaging control unit includes a gate driver that applies gate pulses to a gate of a TFT to switch the TFT, a signal processing circuit that converts the electric charges accumulated in the pixels into analog electrical signals representing an X-ray image and outputs the analog electrical signals, and the like. Further, the housing 82 has substantially the same size as, for example, a film cassette, an imaging plate (IP) cassette, or a computed radiography (CR) cassette that is based on International Organization for Standardization (ISO) 4090:2001.

A transmission plate 83, which transmits radiation, is mounted on the front surface of the housing 82. The transmission plate 83 has a size substantially corresponding to a detection region for radiation of the radiation detector 80, and is made of a carbon material that is light and has high stiffness and high radiotransparency. The shape of the detection region is the same rectangular shape as the shape of the front surface of the housing 82. Further, a portion of the housing 82 corresponding to the frame protrudes from the transmission plate 83 in the thickness direction of the radiation detector 80. For this reason, the transmission plate 83 is not easily damaged.

Markers 84A to 84D, which represent identification information for identifying the radiation detector 80, are given to four corners of the front surface of the housing 82. In this embodiment, the markers 84A to 84D are formed of two bar codes orthogonal to each other, respectively.

Further, a connector 85, which is used to charge the radiation detector 80, is mounted on the side surface of the housing 82 corresponding to the markers 84C and 84D.

In a case in which the radiation-irradiation device 1 according to this embodiment is in use, an operator raises the arm unit 30 relative to the body unit 20 from the initial position of the arm unit 30 shown in FIG. 1 by the raising/lowering mechanism 50. Then, the operator moves the radiation source unit 40 to a target position directly above the subject H as shown in FIG. 2 by rotating the second arm 32 about the rotational movement axis AX2 from an initial rotational state in a counterclockwise direction in FIG. 1 and rotating the first arm 31 about the rotational movement axis AX1 after removing the connecting belt 36. Further, after the radiation source unit 40 is moved to the target position, the radiation source unit 40 is driven by a command sent from the input part 24 and irradiates the subject H with radiation. Then, the radiation transmitted through the subject H is detected by the radiation detector 80, so that the radiation image of the subject H can be acquired.

Figure 8:
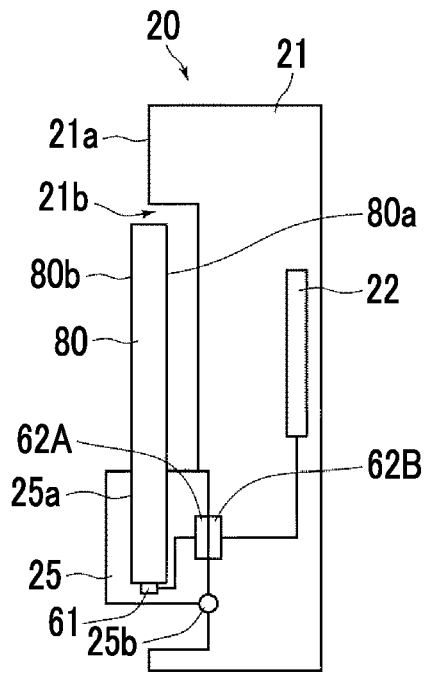
FIG. 8 is a diagram showing a structure that can receive the radiation detector.
Figure 9:
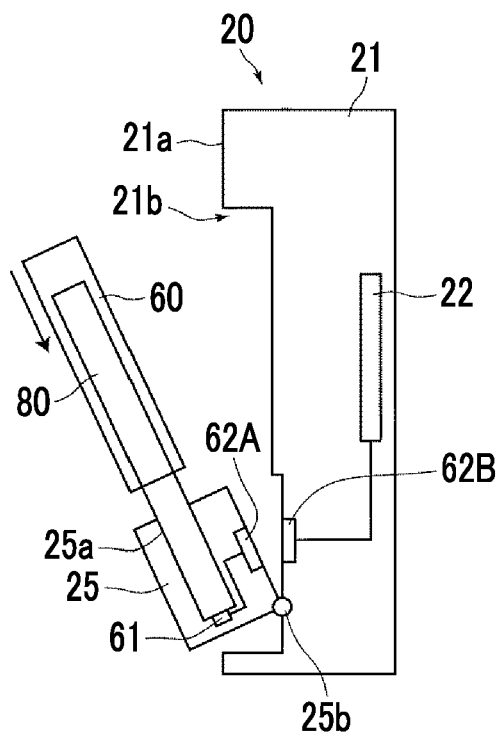
FIG. 9 is a diagram showing the structure that can receive the radiation detector.

Next, the structure of the body unit 20 that can receive the radiation detector 80 will be described. FIG. 8 is a diagram showing the structure that can receive the radiation detector 80. FIG. 8 shows a cross-section that is taken along a y-z plane at a substantially middle position of the housing 21 in a width direction parallel to the x direction. As shown in FIG. 8, the housing 21 includes a flat surface 21a on the surface of the body unit 20 opposite to the side on which the arm unit 30 is mounted. A rectangular recessed portion 21b is formed on the flat surface 21a. The recessed portion 21b has a size that allows the radiation detector 80 to be received in the recessed portion 21b. A cradle 25, which supports one edge portion of the radiation detector 80, is mounted on the lower portion of the recessed portion 21b so as to be capable of being rotationally moved relative to the housing 21 by a hinge 25b extending in the x direction. Accordingly, the cradle 25 is mounted on the housing 21 so as to be movable between a first position which is shown in FIG. 8 and at which the radiation detector 80 is received and a second position which is shown in FIG. 9 and at which the radiation detector 80 is to be mounted on or detached from the cradle 25. The cradle 25 corresponds to a detector holder.

The body unit 20 is formed to be thin so that the length of the body unit 20 in a direction orthogonal to the flat surface 21a, that is, the length of the body unit 20 in the y direction in FIG. 2 is shorter than the length of the body unit 20 in an arbitrary direction parallel to the flat surface 21a, particularly, the x direction and the z direction.

Further, the surface of the cradle 25 is subjected to hydrophilic treatment as disclosed in, for example, JP2015-27416A, and the material of the cradle 25 includes an antimicrobial agent. The type of the antimicrobial agent is not particularly limited, and a publicly known antimicrobial agent can be used. For example, an inorganic antimicrobial agent or an organic antimicrobial agent (preferably, a water-soluble organic antimicrobial agent) may be used as the antimicrobial agent. A material exerting a bactericidal effect against pathogenic bacteria represented by *Staphylococcus aureus* and colon *bacillus* is suitably used as the antimicrobial agent.

An insertion opening 25a into which the radiation detector 80 is to be inserted is formed on the upper surface of the cradle 25. The insertion opening 25a has an elongated shape having a size that allows the radiation detector 80 to be fitted to the insertion opening 25a. In this embodiment, one edge portion of the radiation detector 80 including the connector 85 is inserted into the insertion opening 25a. Accordingly, the one edge portion is supported by the cradle 25, so that the radiation detector 80 is held by the cradle 25. In this case, the front surface of the radiation detector 80 faces the flat surface 21a. In a case in which one edge portion of the radiation detector 80 is supported by the cradle 25, the one edge portion of the radiation detector 80 is positioned on the lower side in the vertical direction and one edge portion thereof opposite to the edge portion is positioned on the upper side in the vertical direction. The depth of the insertion opening 25a is set in the range of about ¼ to ⅓ of the length of the radiation detector 80, that is, the length of each of two edge portions orthogonal to the one edge portion of the radiation detector 80 to be inserted into the insertion opening 25a. In a case in which the cradle 25 is positioned at the first position, the radiation detector 80 is held along the flat surface 21a of the housing 21 by the cradle 25 so that a surface 80a of the radiation detector 80 facing the body unit 20 is received in the recessed portion 21b so as to be closer to the inside of the housing 21 than the flat surface 21a.

In FIG. 8, a surface 80b of the radiation detector 80 opposite to the body unit 20 is positioned closer to the outside than the flat surface 21a, and the surface 80a of the radiation detector 80 facing the body unit 20 is positioned closer to the inside of the housing 21 than the flat surface 21a. However, the cradle 25 may be adapted so that the surface 80b of the radiation detector 80 opposite to the body unit 20 is received in the housing 21 to be closer to the inside of the housing 21 than the flat surface 21a. Further, the cradle 25 may be adapted so that the surface 80b of the radiation detector 80 opposite to the body unit 20 corresponds to the flat surface 21a. Furthermore, the cradle 25 may be adapted so that the surface 80a of the radiation detector 80 facing the body unit 20 is positioned outside the flat surface 21a, and the cradle 25 may be adapted so that the surface 80a of the radiation detector 80 facing the body unit 20 corresponds to the flat surface 21a.

In a case in which the cradle 25 is positioned at the second position, the edge portion of the radiation detector 80 opposite to one edge portion of the radiation detector 80 supported by the cradle 25 is held at a position away from the housing 21. In a case in which the cradle 25 is positioned at the second position, three edge portions of the radiation detector 80 other than the one edge portion of the radiation detector 80 supported by the cradle 25 are in an open state. For this reason, a contamination preventive bag 60, which prevents the contamination of the radiation detector 80, can be easily mounted on the radiation detector 80 as shown in FIG. 9.

On the other hand, a connector 61 is mounted on the bottom portion of the insertion opening 25a of the cradle 25. The connector 61 is electrically connected to the connector 85 of the radiation detector 80 in a case in which the radiation detector 80 is held by the cradle 25. A connector 62A, which is electrically connected to the connector 61, is mounted on the surface of the cradle 25 that comes into contact with the housing 21 in a case in which the cradle 25 is positioned at the first position. A connector 62B, which is electrically connected to the control unit 22, is mounted on the housing 21 at a position facing the connector 62A in a case in which the cradle 25 is positioned at the first position. The surfaces, which face each other, of the connectors 62A and 62B are formed of flat surfaces. Further, the connectors 62A and 62B are electrically connected to each other in a case in which the cradle 25 is positioned at the first position. The connectors 62A and 62B are separated from each other in a case in which the cradle 25 is positioned at a position other than the first position. Accordingly, in a case in which the cradle 25 is positioned at the first position and the connector 13 mounted on the leg unit 10 is connected to the power source, the radiation detector 80 can be charged through the control unit 22. In this case, the device 1 itself can also be charged. Further, since the connectors 62A and 62B are separated from each other and the electrical connection between the connectors 62A and 62B is released in a case in which the cradle 25 is moved from the first position, the charging of the radiation detector 80 can be released.

The electrical connection between the connectors 62A and 62B is not limited to a case in which the cradle 25 is moved to the first position, and the connectors 62A and 62B may be electrically connected to each other in at least a case in which the cradle 25 is moved to the first position. Further, the release of the electrical connection between the connectors 62A and 62B is not limited to a case in which the cradle 25 is moved to a position other than the first position, and the electrical connection between the connectors 62A and 62B may be released in at least a case in which the cradle 25 is moved to the second position.

Here, in this embodiment, the charging mode of the radiation detector 80 can be changed by a command sent from the input part 24. For example, in this embodiment, the charging mode can be switched to a normal charging mode that is used to fully charge the battery of the radiation detector 80 with time and a fast charging mode that is used not to fully charge the battery of the radiation detector 80 but to charge the battery of the radiation detector 80 in a short time.

In this embodiment, as described above, the cradle 25 supports one edge portion of the radiation detector 80 having the shape of a rectangular flat plate and is mounted on the body unit 20 so as to be movable between the first position at which the radiation detector 80 is held along the flat surface 21a of the body unit 20 and the second position at which an edge portion of the radiation detector 80 opposite to one edge portion of the radiation detector 80 is held at a position away from the body unit 20. For this reason, in a case in which the cradle 25 is moved to the second position, one edge portion of the radiation detector 80 can be supported by the cradle 25. After that, in a case in which the cradle 25 is moved to the first position, the radiation detector 80 is held along the flat surface 21a of the body unit 20. For this reason, the radiation detector 80 can be held integrally with the body unit 20. Accordingly, an increase in the size of the device 1 can be prevented while the device 1 receives the radiation detector 80. Therefore, the device 1 can perform imaging in a small radius while receiving the radiation detector 80.

The cradle 25 may be adapted to be detachable from the housing 21. Accordingly, the cradle can be replaced with cradles having sizes suitable for holding radiation detectors 80 having various sizes, such as a size of 17×17, a size of 17×14, and a mini size. The unit of the numerical value of the size of the radiation detector 80 is inch. Further, in a case in which the cradle 25 is contaminated, the cradle 25 is detached and can be easily washed.

Figure 10:
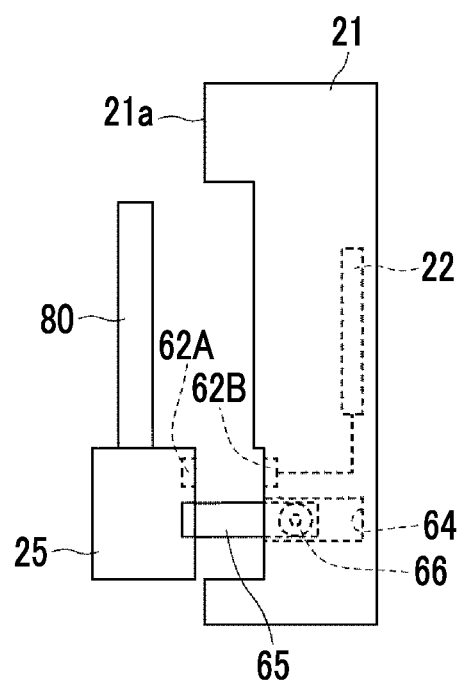
FIG. 10 is a diagram showing the structure that can receive the radiation detector.

Furthermore, in the first embodiment, the cradle 25 is mounted on the housing 21 so as to be capable of being moved to the first and second positions by the hinge 25b. However, the cradle 25 may be adapted to be moved in a direction orthogonal to the flat surface 21a of the housing 21. That is, as shown in FIG. 10, a rail 64 is mounted on the cradle 25 and a rail 65 is mounted on the housing 21 at a position corresponding to the cradle 25. A roller 66 is mounted on the distal end of the rail 65. The rail 65 is fitted to the rail 64 and can slide relative to the rail 64. Meanwhile, a stopper (not shown) is mounted on the rail 65 so that the rail 65 does not easily deviate from the rail 64.

Accordingly, the cradle 25 is mounted on the housing 21 so as to be movable between a first position at which the radiation detector 80 is held along the flat surface 21a of the housing 21 and a second position at which one edge portion of the radiation detector 80 and an edge portion of the radiation detector 80 opposite to the one edge portion are held at positions away from the housing 21. Even in a case in which the cradle 25 is mounted on the housing 21 as described above, an increase in the size of the device can be prevented while the device 1 receives the radiation detector 80 as in the first embodiment. As a result, the device 1 can perform imaging in a small radius while receiving the radiation detector 80. Further, a contamination preventive bag for prevention of infection can be easily mounted on the radiation detector 80 in a state in which the cradle 25 is moved to the second position.

Figure 11:
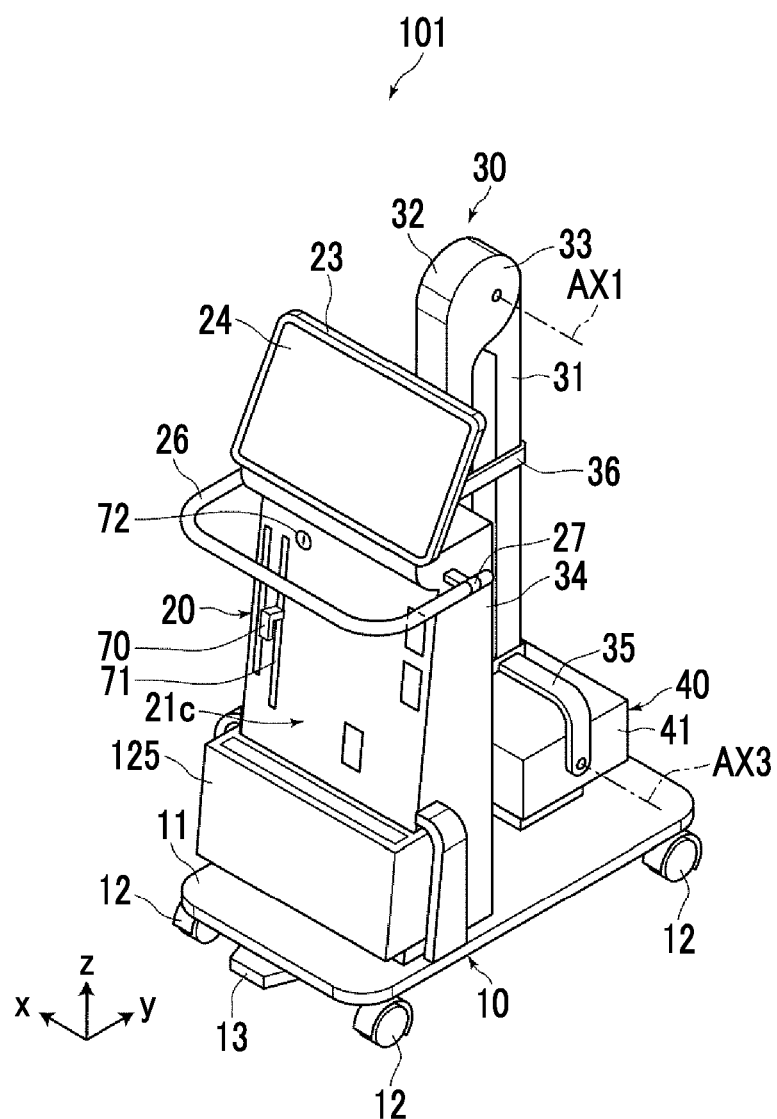
FIG. 11 is a perspective view showing the shape of the entire radiation-irradiation device according to a second embodiment of the invention.
Figure 12:
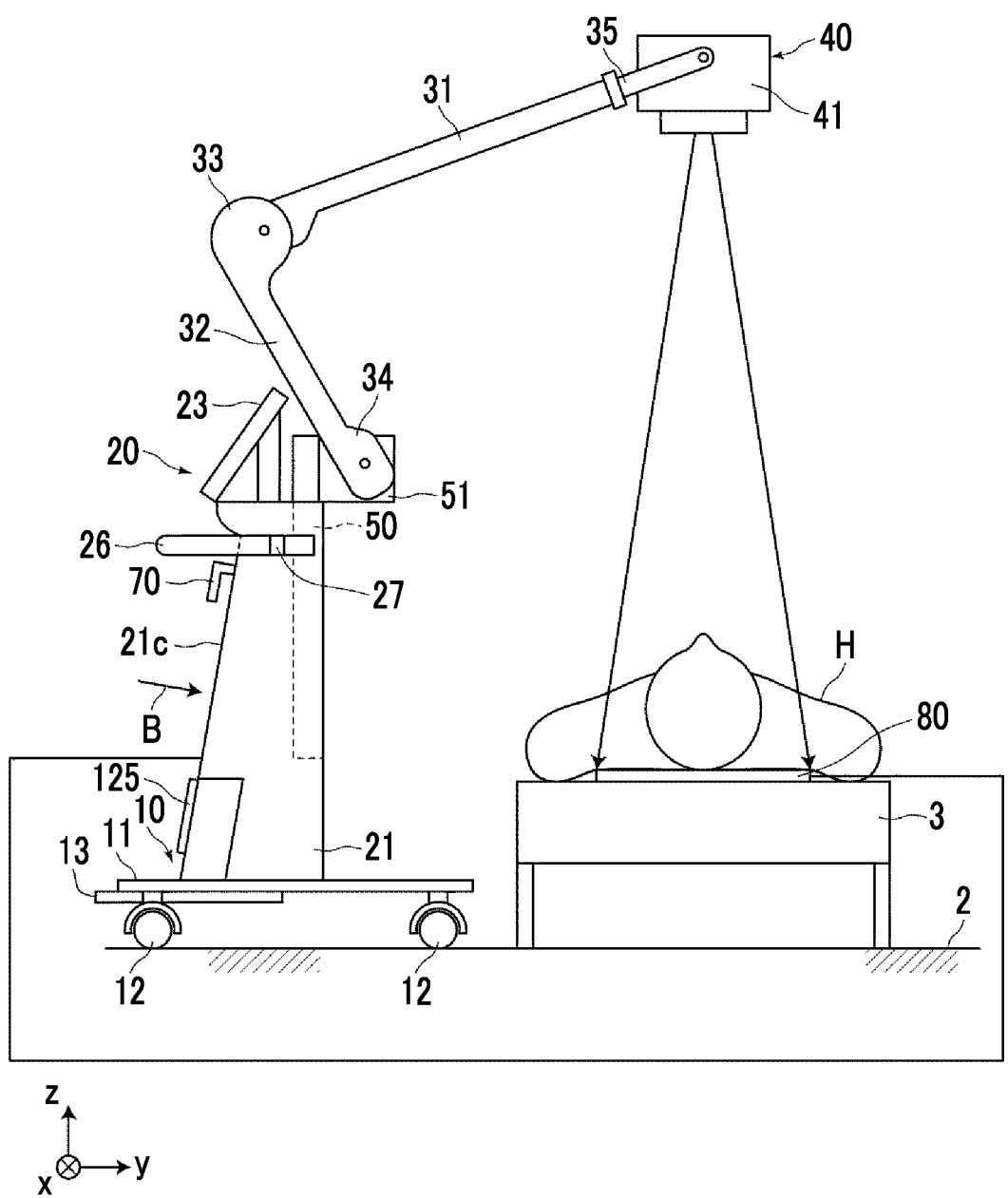
FIG. 12 is a diagram showing a state in which the radiation-irradiation device according to the second embodiment of the invention is in use.
Figure 13:
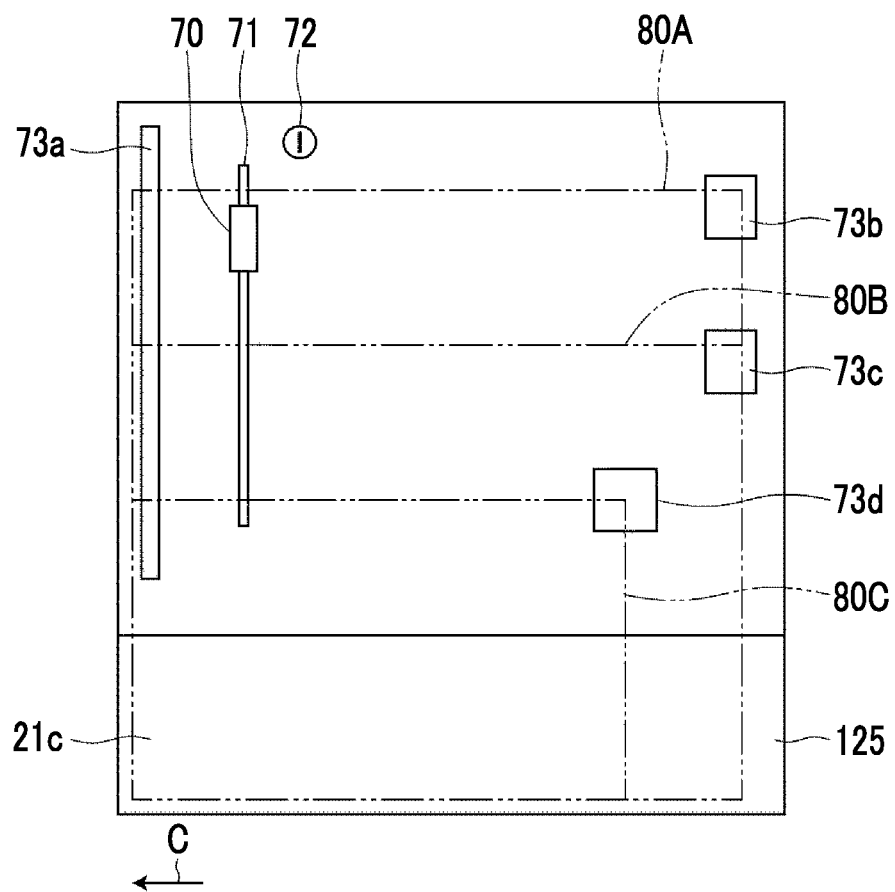
FIG. 13 is a diagram viewed in the direction of arrow B of FIG. 12.

Next, a second embodiment of the invention will be described. FIG. 11 is a perspective view showing the shape of the entire radiation-irradiation device according to a second embodiment of the invention in a case in which the radiation-irradiation device is not in use, FIG. 12 is a side view showing a state in which the radiation-irradiation device according to the second embodiment of the invention is in use, and FIG. 13 is a diagram viewed in the direction of arrow B of FIG. 12. The same components of FIGS. 11 to 13 as the components of FIGS. 1 and 2 are denoted by the same reference numerals as the reference numerals of FIGS. 1 and 2, and the detailed description thereof will be omitted. A radiation-irradiation device 101 according to the second embodiment is different from the first embodiment in that a housing 21 of a body unit 20 includes a flat surface 21c, which is inclined toward an arm unit 30, on the surface of the body unit 20 opposite to the side on which the arm unit 30 is mounted and includes a cradle 125 having a structure different from the structure of the cradle 25 of the first embodiment. Here, the flat surface 21c is inclined so as to be close to the side of the housing 21 to which the arm unit 30 is connected as the flat surface 21c is away from a leg unit 10 in a z direction. In detail, in a case in which a perpendicular extending from a portion, which is connected to the leg unit 10, of the flat surface 21c of the housing 21 in the z direction is prescribed in FIG. 12, the flat surface 21c is inclined so as to be away from the perpendicular as the flat surface 21c is away from the leg unit 10 in the z direction.

In the second embodiment, the recessed portion 21b of the first embodiment is not formed on the flat surface 21c. As a result, a radiation detector 80 is held by the cradle 125 so that the surface of the radiation detector 80 facing the body unit 20 is positioned outside the flat surface 21c of the housing 21. Further, omnidirectional cameras 28 are omitted in FIGS. 11 and 12. Furthermore, it is preferable that the inclination angle of the flat surface 21c relative to the z axis is in the range of about 5 to 10°.

Moreover, the radiation-irradiation device 101 according to the second embodiment includes a fixing part 70 that fixes an upper edge portion of the radiation detector 80 to the flat surface 21c in a case in which the cradle 125 is positioned at the first position. The fixing part 70 has the shape of a key that is engaged with the upper edge portion of the radiation detector 80. Further, the fixing part 70 is mounted on the flat surface 21c so as to be movable on the flat surface 21c in the vertical direction. Specifically, a guide hole 71, which extends in the vertical direction, is formed on the flat surface 21c, and the fixing part 70 is mounted on the flat surface 21c so as to be frictionally engaged with the guide hole 71. For this reason, the fixing part 70 can be stopped at an arbitrary position in the guide hole 71. Accordingly, the fixing part 70 can be moved to the positions of upper edge portions of radiation detectors 80 having various sizes and can fix the radiation detectors 80 to the flat surface 21c.

Further, the radiation-irradiation device 101 according to the second embodiment includes a locking part 72 that locks the fixing part 70 to restrict the movement of the fixing part 70. The locking part 72 locks the fixing part 70 in a case in which the movement of the fixing part 70 along the guide hole 71 is restricted by a key. The locking part 72 may be adapted to perform locking using a key, may be adapted to perform locking using a password, or may be adapted to perform locking using the biometric authentication or the like of a fingerprint, the iris, or the like. Accordingly, since the fixing part 70 is locked in a state in which the fixing part 70 fixes the opposite edge portion of the radiation detector 80 to the flat surface 21c, the radiation detector 80 fixed to the flat surface 21c does not deviate from the fixing part 70. Therefore, the theft of the radiation detector 80 held by the cradle 125 can be prevented.

Further, the radiation-irradiation device 101 according to the second embodiment includes cushioning materials 73a, 73b, 73c, and 73d that are provided at four positions on the flat surface 21c. The cushioning materials 73a, 73b, 73c, and 73d are formed of, for example, rubber, foamed styrol, shock-absorbing gel, and the like, and are provided on the flat surface 21c at positions facing the radiation detector 80. More specifically, the cushioning material 73a is provided on the flat surface 21c so as to extend in the vertical direction at the left end of the flat surface 21c shown in FIG. 13. Here, in the second embodiment, the radiation detector 80 is held by the cradle 125 so that the front surface of the radiation detector 80, that is, a radiation detecting surface faces the flat surface 21c. Furthermore, the radiation detector 80 held by the cradle 125 is biased in the direction of arrow C shown in FIG. 13 as described below. For this reason, in a case in which the radiation detector 80 is held by the cradle 125, a left end portion of the front surface of the radiation detector 80 in FIG. 13 touches the cushioning material 73a regardless of the size of the radiation detector 80. In the following description, up, down, left, and right represent directions in a case in which the flat surface 21c is viewed in the direction shown in FIG. 13. Further, in a case in which a radiation detector 80A having a size of 17×17 is held by the cradle 125, the cushioning material 73b is provided at a position facing the upper right corner of the front surface of the radiation detector 80A. Furthermore, in a case in which a radiation detector 80B having a size of 17×14 is held by the cradle 125, the cushioning material 73c is provided at a position facing the upper right corner of the front surface of the radiation detector 80B. Moreover, in a case in which a radiation detector 80C having a mini size is held by the cradle 125, the cushioning material 73d is provided at a position facing the upper right corner of the front surface of the radiation detector 80C. The radiation detectors 80A, 80B, and 80C are shown in FIG. 13 by imaginary lines. Further, in the following description, there is a case where the radiation detectors 80A, 80B, and 80C are generically referred to as the radiation detector 80.

Here, the housing 82 of the radiation detector 80 includes a frame made of metal, and a portion of the housing 82 corresponding to the frame protrudes from the transmission plate 83 on the front surface of the radiation detector 80. For this reason, in a case in which the radiation detector 80 is received in the cradle 125 and is moved to the first position, the portion of the radiation detector 80 corresponding to the frame made of metal touches the cushioning materials 73a, 73b, 73c, and 73d.

Figure 14:
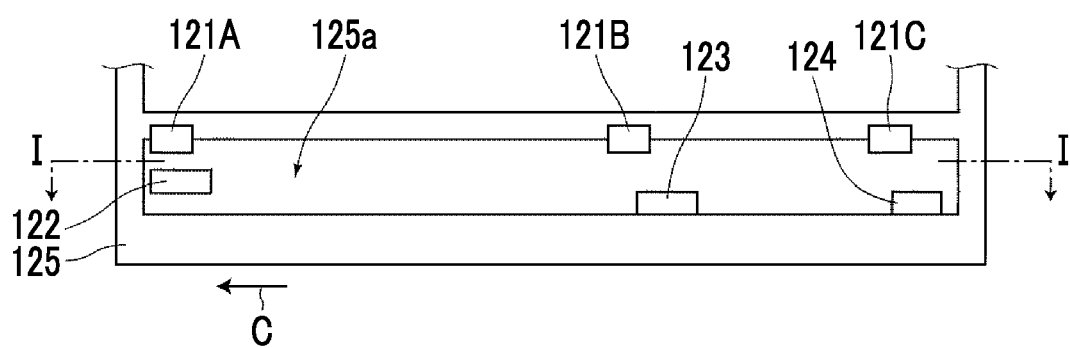
FIG. 14 is a diagram showing a cradle from the upper surface of the cradle.
Figure 15:
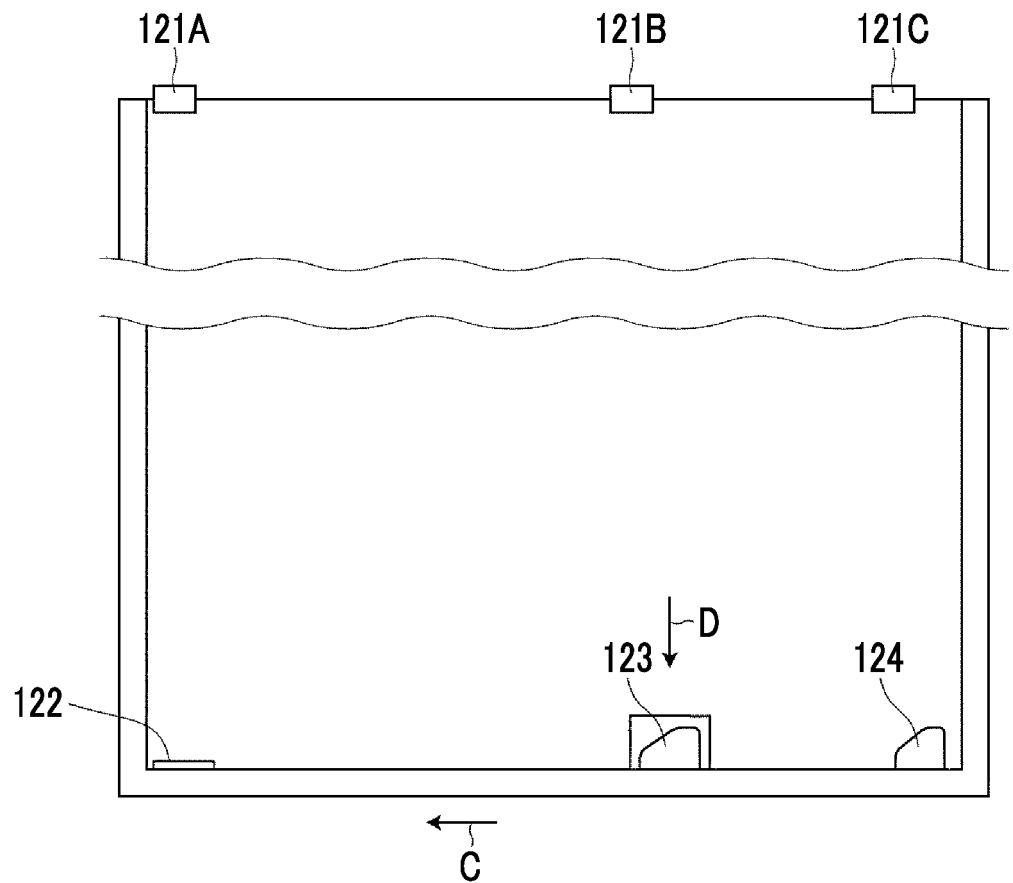
FIG. 15 is a cross-sectional view of the cradle taken along line I-I of FIG. 14.

Next, the structure of the cradle 125 of the second embodiment will be described. FIG. 14 is a diagram showing the cradle from the upper surface of the cradle, and FIG. 15 is a cross-sectional view of the cradle taken along line I-I of FIG. 14. The upper side in FIG. 14 is the side of the housing 21 facing the flat surface 21c. As shown in FIG. 14, three rollers 121A, 121B, and 121C are mounted on the side of an insertion opening 125a of the cradle 125 of the second embodiment facing the flat surface 21c so as to be rotatable about an axis extending in a lateral direction of FIG. 14.

The roller 121A is mounted at a position where the roller 121A touches a left end portion of the front surface of the radiation detector 80 in a case in which the radiation detector 80 having any size is held by the cradle 125. The roller 121B is mounted at a position where the roller 121B touches a right end portion of the front surface of the radiation detector 80C in a case in which the radiation detector 80C having a mini size is held by the cradle 125. The roller 121C is mounted at a position where the roller 121C touches a right end portion of the front surface of each of the radiation detectors 80A and 80B in a case in which each of the radiation detector 80A having a size of 17×17 and the radiation detector 80B having a size of 17×14 is held by the cradle 125. The left end and right end of each of the radiation detectors 80A, 80B, and 80C correspond to a portion of the housing 82 corresponding to the frame. For this reason, the touch between the transmission plate 83 of the radiation detector 80 and the cradle 125 can be prevented since the rollers 121A, 121B, and 121C are mounted in the insertion opening 125a as described above.

Further, a connector 122, which is to be electrically connected to the connector 85 of the radiation detector 80, is mounted on the bottom portion of the cradle 125 near the left end of the bottom portion of the cradle 125. The connector 122 is mounted at a position facing the connector 85 of the radiation detector 80 in a case in which the radiation detector 80 is positioned on the leftmost side of the cradle 125.

Furthermore, a stopper 123 is provided on the bottom portion of the cradle 125 at a position corresponding to the lower right corner of the radiation detector 80C in a case in which the radiation detector 80C having a mini size is held. Further, a stopper 124 is provided on the bottom portion of the cradle 125 at a position corresponding to the lower right corner of each of the radiation detectors 80A and 80B in a case in which each of the radiation detector 80A having a size of 17×17 and the radiation detector 80B having a size of 17×14 is held. The stoppers 123 and 124 are biased in the direction of arrow C shown in FIG. 15. For this reason, in a case in which the radiation detector 80C having a mini size is held by the cradle 125, the lower right corner of the radiation detector 80C touches the stopper 123 and is further biased in the direction of arrow C. Furthermore, in a case in which each of the radiation detector 80A having a size of 17×17 and the radiation detector 80B having a size of 17×14 is held by the cradle 125, the lower right corner of each of the radiation detectors 80A and 80B touches the stopper 124 and is further biased in the direction of arrow C. The stoppers 123 and 124 correspond to a biasing part.

Figure 16:
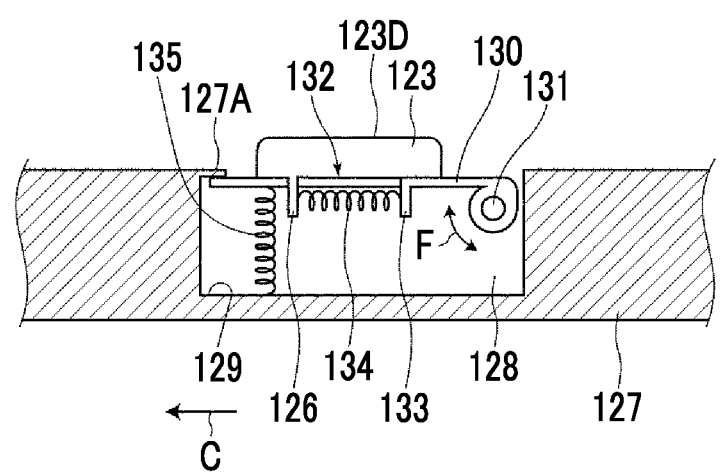
FIG. 16 is a diagram showing the detailed structure of a stopper.

FIG. 16 is a diagram showing the detailed structure of the stopper 123. FIG. 16 is a partial cross-sectional view seen in the direction of arrow D of FIG. 15. As shown in FIG. 16, the stopper 123 is mounted in a recessed portion 128 that is formed on a wall portion 127 of the cradle 125. The wall portion 127 is positioned on the surface of the cradle 125 opposite to the surface of the cradle 125 facing the flat surface 21c. A part of the stopper 123 is mounted on a base 130 that is present in the recessed portion 128. The base 130 is oscillatably mounted on the wall portion 127 by a shaft part 131 extending in the vertical direction in FIG. 15.

Figure 17:
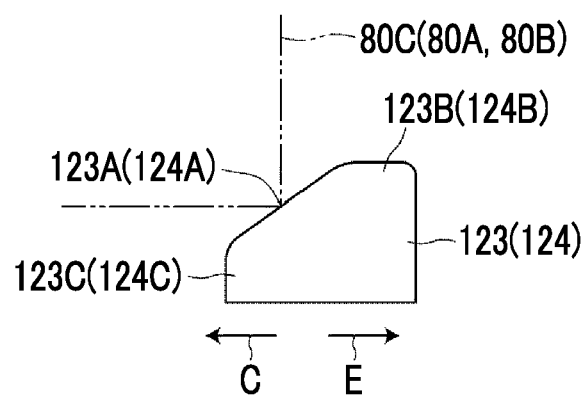
FIG. 17 is a side view of the stopper.

A long hole 132, which extends in the lateral direction in FIG. 16, is formed in the base 130, and a protruding portion 126, which protrudes from the surface of the stopper 123 facing the base 130, is inserted into the long hole 132. A protruding portion 133, which protrudes toward the recessed portion 128, is formed at the right end of the long hole 132 of the base 130 in FIG. 16. A spring 134 is mounted between the protruding portions 126 and 133. Further, a tapered surface 123A, an upper surface 123B, and a side surface 123C, which are smoothly connected to each other, are formed around the stopper 123 as shown in FIG. 17. Round chamfering is performed at side portions 123D where the surface of the stopper 123 opposite to the base 130 crosses the tapered surface 123A, the upper surface 123B, and the side surface 123C.

Furthermore, in a case in which the radiation detector 80C is inserted into the insertion opening 125a of the cradle 125, the lower right corner of the radiation detector 80C touches the tapered surface 123A of the stopper 123. Since the lower right corner of the radiation detector 80C is subjected to round chamfering, the stopper 123 is moved to the right side, that is, in the direction of arrow E of FIG. 17 in a case in which the radiation detector 80C is moved toward the bottom portion. In addition, in a case in which the radiation detector 80C reaches the bottom portion of the cradle 125, the right side surface of the radiation detector 80C touches the side surface 123C of the stopper 123 and the radiation detector 80C is biased to the left side, that is, in the direction of arrow C by the stopper 123.

The structure of the stopper 124 is the same as the structure of the stopper 123 except that the base is adapted to be oscillatable. That is, in a case in which each of the radiation detectors 80A and 80B is inserted into the insertion opening 125a of the cradle 125, the lower right corner of each of the radiation detectors 80A and 80B touches a tapered surface 124A of the stopper 124. Since the lower right corner of each of the radiation detectors 80A and 80B is subjected to round chamfering, the stopper 124 is moved to the right side, that is, in the direction of arrow E of FIG. 17 in a case in which each of the radiation detectors 80A and 80B is moved toward the bottom portion. Then, in a case in which each of the radiation detectors 80A and 80B reaches the bottom portion of the cradle 125, the right side surface of each of the radiation detectors 80A and 80B touches a side surface 124C of the stopper 124 and each of the radiation detectors 80A and 80B is biased to the left side, that is, in the direction of arrow C by the stopper 124.

Accordingly, the connector 85 of the radiation detector 80 is electrically connected to the connector 122 of the cradle 125, so that the radiation detector 80 can be reliably charged. Further, the radiation detector 80 is sandwiched between the stopper 123 or 124 and the left end of the cradle 125 by the biasing force of the spring 134. For this reason, the shake of the radiation detector 80 can be prevented during the movement of the device 101 holding the radiation detector 80. Furthermore, the left end portion of the front surface of the radiation detector 80 touches the cushioning material 73a and the upper right corner of the front surface of the radiation detector 80 touches the cushioning material 73b, 73c, or 73d. For this reason, even though the radiation detector 80 overlaps the flat surface 21c, the touch between the transmission plate 83 of the radiation detector 80 and the flat surface 21c can be prevented.

Further, a spring 135 is mounted between the surface of the base 130 facing the recessed portion 128 and the lower surface of the recessed portion 128 in FIG. 16. The base 130 is biased in the clockwise direction in FIG. 16 by the spring 135. However, since the left end portion of the base 130 touches a protrusion portion 127A formed on the wall portion 127, the base 130 does not protrude outward from the wall portion 127. Here, since the stopper 123 is mounted at a position where the stopper 123 touches the lower right corner of the radiation detector 80C having a mini size, the stopper 123 obstructs the radiation detector in a case in which the radiation detector 80A having a size of 17×17 or the radiation detector 80B having a size of 17×14 is inserted into the cradle 125. However, in a case in which the edge portion of the radiation detector 80A or 80B touches the stopper 123, the lower side of the radiation detector 80A or 80B touches the upper surface 123B of the stopper 123. Here, since the side portions 123D of the stopper 123 are subjected to round chamfering, the base 130 oscillates about the shaft part 131 and the stopper 123 is pushed into the recessed portion 128 of the wall portion 127 in a case in which the radiation detector 80A or 80B is further moved down in the cradle 125. For this reason, the stopper 123 does not obstruct the radiation detector in a case in which the radiation detector 80A or 80B is held by the cradle 125. In a case in which the radiation detector 80A or 80B is detached from the cradle 125, the base 130 is returned to the position shown in FIG. 16 by the biasing force of the spring 135.

Here, each of the cradles 25 and 125 is adapted to hold only a part of the radiation detector 80 so that the radiation detector 80 is easily covered with a contamination preventive bag in a state in which each of the cradles 25 and 125 of the first and second embodiments of the invention holds the radiation detector 80. In a case in which only a part of the radiation detector 80 is held as described above, the radiation detector 80 shakes during the movement of the radiation-irradiation device 101. Since the flat surface 21c of the housing 21 is formed of a surface inclined toward the side to which the arm unit 30 is connected in the second embodiment, the shake of the radiation detector 80 can be prevented in a case in which the radiation-irradiation device 101 is moved in a state in which the radiation detector 80 is held by the cradle 125. Further, since a gap between the flat surface 21c and the radiation detector 80 can be made large in a case in which the cradle 125 is moved to the second position, a contamination preventive bag can be more easily mounted on the radiation detector 80.

Since the radiation-irradiation device further includes the fixing part 70 that fixes an upper edge portion of the radiation detector 80 to the flat surface 21c in a case in which the cradle 125 is positioned at the first position, the shake of the radiation detector 80 can be more reliably prevented in a case in which the radiation-irradiation device 101 is moved in a state in which the radiation detector 80 is held by the cradle 125.

Furthermore, there is a concern about the theft of the radiation detector 80 in a case in which only a part of the radiation detector 80 is held by the cradle 125 as in this embodiment. For this reason, the radiation-irradiation device includes the locking part 72 for locking the fixing part 70. Accordingly, the theft of the radiation detector 80 can be prevented.

Further, the fixing part 70 is mounted on the flat surface 21c so as to be movable on the flat surface 21c in the vertical direction. Accordingly, even though each of radiation detectors 80 having different sizes is held by the cradle 125, the upper edge portion of the radiation detector 80 can be fixed to the flat surface 21c.

The radiation detector 80 has the shape of a rectangular flat plate in each of the embodiments, but may have the shape of a substantially rectangular flat plate. For example, even though one edge portion of the radiation detector does not have the shape of a straight line due to a handle formed on one edge portion of the radiation detector or a notch or a protruding portion formed on one edge portion of the radiation detector, the other three edge portions of the radiation detector have only to be substantially orthogonal to each other. In this case, if one edge portion of the radiation detector not having the shape of a straight line is positioned on the upper side and the other three edge portions of the radiation detector are positioned on the lower side, the other three edge portions of the radiation detector 80 can be held by the cradle 25.

Further, one radiation detector 80 is held by each of the cradles 25 and 125 in each of the embodiments, but each of the cradles 25 and 125 may be adapted to hold a plurality of radiation detectors 80 in accordance with the thickness of the body unit 20. In this case, insertion openings 25a and 125a, of which the numbers correspond to the number of radiation detectors 80 to be held, may be formed in the cradles 25 and 125.

Furthermore, each of the stoppers 123 and 124 is formed in a shape having a tapered surface in the second embodiment, but the tapered surface may be a curved surface. Moreover, the stoppers may be formed in an arbitrary shape that is convex upward.

Further, two stoppers 123 and 124 are mounted at positions corresponding to the size of the radiation detector in the second embodiment. However, in a case in which the size of a radiation detector is only one type, only one stopper may be mounted at a position corresponding to the size of the radiation detector. Furthermore, in a case in which radiation detectors having a plurality of different sizes are used, stoppers may be mounted at a plurality of positions corresponding to the sizes of the radiation detectors.

The effects of the embodiments of the invention will be described below.

Since the detector holder is adapted to hold the radiation detector so that one edge portion of the radiation detector is positioned on the lower side in a vertical direction and the opposite edge portion thereof is positioned on the upper side in the vertical direction, the contamination preventive bag can be easily mounted on the radiation detector from one edge portion of the radiation detector toward the opposite edge portion thereof.

Further, since the body unit is formed so that the length of the body unit in the direction orthogonal to the flat surface is shorter than the length of the body unit in the direction parallel to the flat surface, the body unit can be adapted to be thin in the direction orthogonal to the flat surface. Accordingly, the detector holder is moved to the first position and can hold the radiation detector so that the radiation detector and the body unit can be compactly integrated with each other. Therefore, an increase in the size of the device can be more reliably prevented while the device receives the radiation detector. As a result, the device 1 can perform imaging in a smaller radius while receiving the radiation detector.

Further, since the detector holder holds the radiation detector at least inside the surface of the flat surface at the first position, the detector holder can be moved to the first position to make the body unit, which receives the radiation detector, more compact.

Furthermore, since the detector holder includes the connector that is to be electrically connected to the radiation detector to charge the radiation detector, the radiation detector can be charged in a state in which the radiation detector is received in the body unit.

Moreover, since the connector is electrically connected to the radiation detector at least at the first position and the electrical connection between the connector and the radiation detector is released at least at the second position, the charging of the radiation detector can be released by only an operation for moving the detector holder to the second position from the first position to take the radiation detector out of the body unit.

Further, since there is a possibility that the blood, body fluid, and the like of a patient may be attached to the radiation detector, there is a possibility that the blood, body fluid, and the like of a patient may also be attached to the detector holder. However, since the detector holder is detachably mounted on the body unit, the detector holder is detached from the body unit and can be easily washed in a case in which the detector holder is contaminated. Furthermore, the detector holder is easily replaced with a detector holder that receives a radiation detector having a different size.

Moreover, there is a possibility that the blood, body fluid, and the like of a patient may be attached to the detector holder as described above, but it is possible to prevent the detector holder from being infected with bacteria since the detector holder is subjected to antibacterial treatment.

Further, since the flat surface is formed of a surface inclined toward the side to which the arm unit is connected, the shake of the radiation detector can be prevented in a case in which the radiation-irradiation device is moved in a state in which the radiation detector is held by the detector holder. Furthermore, since a gap between the flat surface and the radiation detector can be made large in a case in which the detector holder is moved to the second position, a contamination preventive bag can be more easily mounted on the radiation detector.

Since the radiation-irradiation device further includes the fixing part that fixes an opposite edge portion of the radiation detector to the flat surface in a case in which the detector holder is positioned at the first position, the shake of the radiation detector can be prevented in a case in which the radiation-irradiation device is moved in a state in which the radiation detector is held by the detector holder.

Further, since the fixing part is mounted on the flat surface so as to be movable on the flat surface in the vertical direction, an opposite edge portion of the radiation detector can be fixed to the flat surface even though each of radiation detectors having different sizes is held by the detector holder.

Since the radiation-irradiation device further includes the locking part for locking the fixing part, the radiation detector cannot be easily detached from the fixing part. Accordingly, the theft of the radiation detector can be prevented.

Furthermore, since the cushioning material is provided on the flat surface at a position facing the radiation detector, damage to the radiation detector can be prevented even though the radiation detector overlaps the flat surface.

Moreover, since the cushioning materials are provided at a plurality of positions corresponding to the sizes of the radiation detectors to be used, damage to the radiation detector can be prevented even though radiation detectors having various sizes are held.

Since the radiation-irradiation device further includes a biasing part for biasing the radiation detector, which is held by the detector holder, along the flat surface in at least one direction orthogonal to one edge portion of the radiation detector, the radiation detector can be held by the detector holder in a state in which the radiation detector is biased in at least one direction. Accordingly, the shake of the radiation detector can be more reliably prevented in a case in which the radiation-irradiation device is moved in a state in which the radiation detector is held by the detector holder.

What is claimed is:

1. A radiation-irradiation device comprising:
    a leg unit, including a platform and wheels, that is capable of traveling on a device-placement surface;
    a radiation source that generates radiation;
    an arm unit on which the radiation source is mounted;
    a body unit to which the arm unit is connected and which is held by the leg unit and includes a flat surface on a side thereof opposite to a side to which the arm unit is connected; and
    a detector holder configured to support one edge portion of a radiation detector that is to be used for detecting the radiation, said detector holder having a shape of a rectangular flat plate and is mounted on the body unit so as to be movable between a first position at which the radiation detector is to be held along the flat surface of the body unit and a second position at which at least an opposite edge portion of the radiation detector opposite to the one edge portion of the radiation detector is to be held at a position away from the body unit;
    wherein the flat surface is inclined toward a side to which the arm unit is connected.

2. The radiation-irradiation device according to claim 1, wherein the detector holder holds the radiation detector so that the one edge portion is positioned on a lower side in a vertical direction and the opposite edge portion of the radiation detector is positioned on an upper side in the vertical direction.

3. The radiation-irradiation device according to claim 1, wherein a length of the body unit in a direction orthogonal to the flat surface is shorter than a length of the body unit in a direction parallel to the flat surface.

4. The radiation-irradiation device according to claim 1, wherein the detector holder holds the radiation detector at least inside a surface of the flat surface at the first position.

5. The radiation-irradiation device according to claim 1, wherein the detector holder is mounted on the body unit so as to be rotationally movable about a rotational movement axis parallel to a direction in which the one edge portion extends.

6. The radiation-irradiation device according to claim 1, wherein the detector holder is mounted on the body unit so as to be movable in a direction orthogonal to a direction in which the one edge portion extends.

7. The radiation-irradiation device according to claim 1, wherein the detector holder includes a connector that is to be electrically connected to the radiation detector to charge the radiation detector.

8. The radiation-irradiation device according to claim 7, wherein the connector is electrically connected to the radiation detector at least at the first position, and electrical connection between the connector and the radiation detector is released at least at the second position.

9. The radiation-irradiation device according to claim 1, wherein the detector holder is detachably mounted on the body unit.

10. The radiation-irradiation device according to claim 1, wherein the detector holder is subjected to antibacterial treatment.

11. The radiation-irradiation device according to claim 1, further comprising:
    a fixing part that fixes the opposite edge portion of the radiation detector to the flat surface in a case in which the detector holder is positioned at the first position.

12. The radiation-irradiation device according to claim 11, wherein the fixing part is mounted on the flat surface so as to be movable on the flat surface in a vertical direction.

13. The radiation-irradiation device according to claim 11, further comprising:
    a lock that locks the fixing part to restrict a movement of the fixing part.

14. The radiation-irradiation device according to claim 1, further comprising
    a cushioning material provided on the flat surface of the body unit at a position facing the radiation detector.

15. The radiation-irradiation device according to claim 14, wherein the cushioning material is provided at a position facing at least a part of the radiation detector around the radiation detector.

16. The radiation-irradiation device according to claim 15,
wherein the cushioning material is provided at a plurality of positions corresponding to sizes of the radiation detectors to be used.

17. The radiation-irradiation device according to claim 1, wherein the detector holder has at least one side portion facing another edge portion of the radiation detector that is orthogonal to the one edge portion of the radiation detector, the radiation detector being held by the detector holder,
wherein the radiation-irradiation device further comprises at least one stopper that biases the radiation detector, which is held by the detector holder, in a direction of the side portion of the detector holder.

18. The radiation-irradiation device according to claim 17,
wherein the at least one stopper comprises a plurality of stoppers, wherein the plurality of stoppers are provided so as to correspond to radiation detectors having a plurality of sizes.

* * * * *